US012605352B2

(12) United States Patent
Murugesan et al.

(10) Patent No.: US 12,605,352 B2
(45) Date of Patent: Apr. 21, 2026

(54) COMPOSITIONS AND METHODS FOR INHIBITING BLOOD CANCER CELL GROWTH

(71) Applicants: UNIVERSITY OF NEW BRUNSWICK, Fredericton (CA); UNIVERSITÉ DE MONCTON, Moncton (CA)

(72) Inventors: Alli Murugesan, Saint John (CA); Anthony Reiman, Saint John (CA); Mohamed Touaibia, Dieppe (CA)

(73) Assignee: THE UNIVERSITY OF NEW BRUNSWICK, Fredericton (CA)

( * ) Notice: Subject to any disclaimer, the term of this patent is extended or adjusted under 35 U.S.C. 154(b) by 1066 days.

(21) Appl. No.: 17/604,508

(22) PCT Filed: Apr. 20, 2020

(86) PCT No.: PCT/CA2020/050523

§ 371 (c)(1),
(2) Date: Oct. 18, 2021

(87) PCT Pub. No.: WO2020/210920

PCT Pub. Date: Oct. 22, 2020

(65) Prior Publication Data

US 2022/0211653 A1 Jul. 7, 2022

Related U.S. Application Data

(60) Provisional application No. 62/836,039, filed on Apr. 18, 2019.

(51) Int. Cl.
*A61K 31/216* (2006.01)
*A61K 31/075* (2006.01)
*A61K 31/12* (2006.01)
*A61K 31/165* (2006.01)

(52) U.S. Cl.
CPC .......... *A61K 31/216* (2013.01); *A61K 31/075* (2013.01); *A61K 31/12* (2013.01); *A61K 31/165* (2013.01)

(58) Field of Classification Search
CPC .......................... A61K 31/216; A61K 47/6911
See application file for complete search history.

(56) References Cited

U.S. PATENT DOCUMENTS

| | | | |
|---|---|---|---|
| 5,981,583 | A | 11/1999 | Aggarwal et al. |
| 8,450,337 | B2 | 5/2013 | Priebe et al. |
| 12,201,599 | B2 | 1/2025 | Murugesan et al. |
| 2017/0042865 | A1 | 2/2017 | Zaid et al. |

FOREIGN PATENT DOCUMENTS

| | | |
|---|---|---|
| CN | 107157978 | 9/2017 |
| JP | 2003119169 | 4/2003 |
| JP | 2010180167 | 8/2010 |
| WO | 2017147718 | 9/2017 |
| WO | 2019075549 A1 | 4/2019 |

OTHER PUBLICATIONS

Qian, Yiping et al., Shengwu Wuli Xuebao (2010), 26(4) pp. 294-300.*

Abdi J, Chen G, Chang H. (2013) Drug resistance in multiple myeloma: latest findings and new concepts on molecular mechanisms. Oncotarget: 4: 2186-2207.

Armutcu, F., Akyol, S., Ustunsoy, S., & Turan, F. F. (2015). Therapeutic potential of caffeic acid phenethyl ester and its anti-inflammatory and immunomodulatory effects (Review). Experimental and Therapeutic Medicine, 9(5), 1582-1588. http://doi.org/10.3892/etm.2015.2346.

Bai B, Wu S, Wang R, Xu J, and Chen L, Bone marrow IRF4 level in multiple myeloma: an indicator of peripheral blood Th17 and disease. Oncotarget, 2017, vol. 8, (49), pp. 85392-85400.

Bertrand E, Jouy N, Manier S, Fouquet G, Guidez S, Boyle E, Noel S, Tomowiak C, Herbaux C, Schraen S, Preudhomme C, Quesnel B, Poulain S and Leleu X, Role of IRF4 in resistance to immunomodulatory (IMid) compounds in Waldenström's macroglobulinemia. Oncotarget, 2017, vol. 8, (68), pp. 112917-112927.

Bjorklund CC, Ma W, Wang ZQ, Davis RE, Kuhn DJ, Kornblau SM, et al. Evidence of a role for activation of Wnt/beta-catenin signaling in the resistance of plasma cells to lenalidomide. J Biol Chem. 2011; 286: 11009-11020.

Boddicker, R. L., Kip, N. S., Xing, X., Zeng, Y., Yang, Z.-Z., Lee, J.-H., . . . Feldman, A. L. (2015). The oncogenic transcription factor IRF4 is regulated by a novel CD30/NF-KB positive feedback loop in peripheral T-cell lymphoma. Blood, 125(20), 3118-27. http://doi.org/10.1182/blood-2014-05-578575.

Chesi, M., et al., The t(4;14) translocation in myeloma dysregulates both FGFR3 and a novel gene, MMSET, resulting in IgH/MMSET hybrid transcripts. Blood, 1998a. 92(9): p. 3025-34.

Chesi, M., et al., Dysregulation of cyclin D1 by translocation into an IgH gamma switch region in two multiple myeloma cell lines. Blood, 1996. 88(2): p. 674-81.

Chesi, M., et al., Frequent dysregulation of the c-maf proto-oncogene at 16q23 by translocation to an Ig locus in multiple myeloma. Blood, 1998b. 91(12): p. 4457-63.

Do, T. N., Ucisik-Akkaya, E., Davis, C. F., Morrison, B. A., & Dorak, M. T. (2010). An intronic polymorphism of IRF4 gene influences gene transcription in vitro and shows a risk association with childhood acute lymphoblastic leukemia in males. Biochimica et Biophysica Acta, 1802(2), 292-300. http://doi.org/10.1016/j.bbadis.2009.10.015.

(Continued)

*Primary Examiner* — Paul V Ward
(74) *Attorney, Agent, or Firm* — Eugene Derenyi; Fogler, Rubinoff LLP

(57) ABSTRACT

Methods, compositions and uses for inhibiting the growth in blood cancer cells in a patient with one or more of a caffeic acid phenpropyl ester (GL8) analogue selected from the group consisting of As26, J229, J91, LL27, LL23, HM7, As25, MT26, and J205. The blood cancer cells can be myeloma, lymphoma and leukemia cells. The methods, compositions and uses can be in conjunction with the use of an IMiD to treat a patient. The compositions can include a pharmaceutically acceptable carrier, adjuvant or vehicle, a pharmaceutically acceptable salt or dietary supplement.

22 Claims, 9 Drawing Sheets

(56) References Cited

OTHER PUBLICATIONS

Fesen, M. R., Pommier, Y., Leteurtre, F., Hiroguchi, S., Yung, J., & Kohn, K. W. (1994). Inhibition of HIV-1 integrase by flavones, caffeic acid phenethyl ester (CAPE) and related compounds. Biochemical Pharmacology, 48(3), 595-608. Retrieved from http://www.ncbi.nlm.nih.gov/pubmed/7520698.
Greenberg, A., Walters, D., Kumar, S., Rajkumar V., Jelinek, D., Responsiveness of cytogenetically discrete human myeloma cell lines to lenalidomide: Lack of correlation with cereblon and interferon regulatory factor 4 expression levels. Eur J Haematol. Dec. 2013; 91(6): doi:10.1111/ejh.12192.
Lopez-Girona A, Mendy D, Ito T, Miller K, Gandhi AK, Kang J. (2012). Cereblon is a direct protein target for immunomodulatory and antiproliferative activities of lenalidomide and pomalidomide. Leukemia, 26: 2326-2335.
Hans, C. P., Weisenburger, D. D., Greiner, T. C., Gascoyne, R. D., Delabie, J., Ott, G., . . . Chan, W. C. (2004). Confirmation of the molecular classification of diffuse large B-cell lymphoma by immunohistochemistry using a tissue microarray. Blood, 103(1), 275-82. http://doi.org/10.1182/blood-2003-05-1545.
Hengeveld, P. J., & Kersten, M. J. (2015). B-cell activating factor in the pathophysiology of multiple myeloma: a target for therapy? Blood Cancer Journal, 5, e282. http://doi.org/10.1038/bcj.2015.3.
Tida, S., Rao, P. H., Butler, M., Corradini, P., Boccadoro, M., Klein, B., . . . Dalla-Favera, R. (1997). Deregulation of MUM1/IRF4 by chromosomal translocation in multiple myeloma. Nature Genetics, 17(2), 226-30. http://doi.org/10.1038/ng1097-226.
Ito T, Ando H, Suzuki T, Ogura T, Hotta K . . . Handa H. (2010) dentification of a primary target of thalidomide teratogenicity. Science. Mar. 12;327(5971):1345 50.
Jost, P. J., & Ruland, J. (2007). Aberrant NF-kappaB signaling in lymphoma: mechanisms, consequences, and therapeutic implications. Blood, 109(7), 2700-7. http://doi.org/10.1182/blood-2006-07-025809.
Klein, U., Casola, S., Cattoretti, G., Shen, Q., Lia, M., Mo, T., . . . Dalla-Favera, R. (2006). Transcription factor IRF4 controls plasma cell differentiation and class-switch recombination. Nature Immunology, 7(7), 773-82. http://doi.org/10.1038/ni1357.
Kyle, RA, Gertz, MA, Witzig, TE, et al. Review of 1027 patients with newly diagnosed multiple myeloma. Mayo Clinic Proceedings 2003;78(1):21-33.
Larki-Harchegani, A., Hemmati, A. A., Arzi, A., Ghafurian-Boroojerdnia, M., Shabib, S., Zadkarami, M. R., & Esmaeilzadeh, S. (2013). Evaluation of the Effects of Caffeic Acid Phenethyl Ester on Prostaglandin E2 and Two Key Cytokines Involved in Bleomycin-induced Pulmonary Fibrosis. Iranian Journal of Basic Medical Sciences, 16(7), 850-7. Retrieved from http://www.ncbi.nlm.nih.gov/pubmed/23997916.
Marriott JB, Muller G, Stirling D, Dalgleish AG. (2001) Immunotherapeutic and antitumour potential of thalidomide analogues. Expert Opin Biol Ther., Jul; 1(4):675-82.
Matsui W, Wang Q, Barber JP, Brennan S, Smith BD, Borrello I, et al. Clonogenic multiple myeloma progenitors, stem cell properties, and drug resistance. Cancer Res. 2008; 68: 190-197.
Morgan GJ, Walker BA, Davies FE. (2012). The genetic architecture of multiple myeloma. Nat Rev Cancer, 12: 335-348.
Natarajan, K., Singh, S., Burke, T. R., Grunberger, D., & Aggarwal, B. B. (1996). Caffeic acid phenethyl ester is a potent and specific inhibitor of activation of nuclear transcription factor NF-kappa B. Proceedings of the National Academy of Sciences of the United States of America, 93(17), 9090-5. Retrieved from http://www.ncbi.nlm.nih.gov/pubmed/8799159.
Nishida, K., et al., The Ig heavy chain gene is frequently involved in chromosomal translocations in multiple myeloma and plasma cell leukemia as detected by in situ hybridization. Blood, 1997. 90(2): p. 526-34.
Odqvist, L., Sánchez-Beato, M., Montes-Moreno, S., Martín-Sanchez, E., Pajares, R., Sánchez-Verde, L., . . . Piris, M. A. (2013). NIK controls classical and alternative NF-κB activation and is necessary for the survival of human T-cell lymphoma cells. Clinical Cancer Research : An Official Journal of the American Association for Cancer Research, 19 (9), 2319-30. http://doi.org/10.1158/1078-0432.CCR-12-3151.
Okutan, H., Ozcelik, N., Yilmaz, H. R., & Uz, E. (2005). Effects of caffeic acid phenethyl ester on lipid peroxidation and antioxidant enzymes in diabetic rat heart. Clinical Biochemistry, 38(2), 191-6. http://doi.org/10.1016/j.clinbiochem.2004.10.003.
Onori, P.; DeMorrow, S.; Gaudio, E.; Franchitto, A.; Mancinelli, R.; Venter, J.; Kopriva, S.; Ueno, Y.; Alvaro, D.; Savage, J.; et al. Caffeic acid phenethyl ester decreases cholangiocarcinoma growth by inhibition of NF-κB and induction of apoptosis. Int. J. Cancer 2009, 125, 565-576.
Patel, S. (2016). Emerging Adjuvant Therapy for Cancer: Propolis and its Constituents. Journal of Dietary Supplements, 13(3), 245-68. http://doi.org/10.3109/19390211.2015.1008614.
Rajkumar SV. Multiple myeloma: 2014 update on diagnosis, risk-stratification, and management. Am J Hematol 2014;89(10):998-1009.
Rajkumar SV, Hayman SR, Lacy MQ, Dispenzieri A Gertz MA. (2005) Blood. Combination therapy with lenalidomide plus dexamethasone (Rev/Dex) for newly diagnosed myeloma. Blood, Dec. 15;106(13):4050-3. Epub Aug. 23, 2005.
Ryu, D., Kim, H. J., Joung, J.- G., Lee, H.-O., Bae, J. S., Kim, S. J., . . . Kim, K. (2014). Comprehensive genomic profiling of IgM multiple myeloma identifies IRF4 as a prognostic marker. Oncotarget, 7(30). http://doi.org/10.18632/oncotarget.9478.
Saito, M., Gao, J., Basso, K., Kitagawa, Y., Smith, P. M., Bhagat, G., . . . Dalla-Favera, R. (2007). A signaling pathway mediating downregulation of BCL6 in germinal center B cells is blocked by BCL6 gene alterations in B cell lymphoma. Cancer Cell, 12(3), 280-92. http://doi.org/10.1016/j.ccr.2007.08.011.
Sanderson, J. T., Clabault, H., Patton, C., Lassalle-Claux, G., Jean-François, J., Paré, A. F., . . . Touaibia, M. (2013). Antiproliferative, antiandrogenic and cytotoxic effects of novel caffeic acid derivatives in LNCaP human androgen-dependent prostate cancer cells. Bioorganic & Medicinal Chemistry, 21(22), 7182-93. http://doi.org/10.1016/j.bmc.2013.08.057.
Shaffer, A. L., Emre, N. C. T., Lamy, L., Ngo, V. N., Wright, G., Xiao, W., . . . Staudt, L. M. (2008). IRF4 addiction in multiple myeloma. Nature, 454(7201), 226-31. http://doi.org/10.1038/nature07064.
Shaughnessy, J., Jr., et al., Cyclin D3 at 6p21 is dysregulated by recurrent chromosomal translocations to immunoglobulin loci in multiple myeloma. Blood, 2001. 98(1): p. 217-23.
Shen, H., Yamashita, A., Nakakoshi, M., Yokoe, H., Sudo, M., Kasai, H., . . . Moriishi, K. (2013). Inhibitory effects of caffeic acid phenethyl ester derivatives on replication of hepatitis C virus. PloS One, 8(12), e82299. http://doi.org/10.1371/journal.pone.0082299.
Singhal S, Mehta J, Desikan R, Ayers D, Roberson P Barlogie B. (1999) Antitumor activity of thalidomide in refractory multiple myeloma. N Engl J Med. Nov. 18;341(21):1565-71.
Sy, L. B., Yang, L.-K., Chiu, C.-J., & Wu, W.-M. (2011). The immunoregulatory effects of caffeic acid phenethyl ester on the cytokine secretion of peripheral blood mononuclear cells from asthmatic children. Pediatrics and Neonatology, 52(6), 327-31. http://doi.org/10.1016/j.pedneo.2011.08.005.
Szliszka, E., Czuba, Z. P., Bronikowska, J., Mertas, A., Paradysz, A., & Krol, W. (2011). Ethanolic Extract of Propolis Augments TRAIL-Induced Apoptotic Death in Prostate Cancer Cells. Evidence-Based Complementary and Alternative Medicine: eCAM, 2011, 535172. http://doi.org/10.1093/ecam/nep180.
Toman I, Loree J, Klimowicz AC, Bahlis N, Lai R, Belch A, Pilarski L, Reiman T. (2011). Expression and prognostio significance of Oct2 and Bob1 in multiple myeloma: implications for targeted therapeutics. Leuk Lymphoma 52(4):659-67. doi: 10.3109/10428194.2010.548535.
Turesson, I., et al., Patterns of improved survival in patients with multiple myeloma in the twenty-first century: a population-based study. Journal of clinical oncology : official journal of the American Society of Clinical Oncology, 2010. 28(5): p. 830-4.

(56) References Cited

OTHER PUBLICATIONS

Wang, L., Chu, K., Liang, Y., Lin, Y., & Chiang, B. (2010). Caffeic acid phenethyl ester inhibits nuclear factor-kappaB and protein kinase B signalling pathways and induces caspase-3 expression in primary human CD4+ T cells. Clinical and Experimental Immunology, 160(2), 223-32. http://doi.org/10.1111/j.1365-2249.2009.04067.x.

Wang L, Yao ZQ, Moorman JP, Xu Y, Ning S (2014) Gene Expression Profiling Identifies IRF4-Associated Molecular Signatures in Hematological Malignancies. PLoS ONE 9(9): e106788. doi:10.1371/journal.pone.0106788.

Wang L, Toomey NL, Diaz LA, Walker G, Ramos JC, et al. (2011) Oncogenic IRFs provide a survival advantage for EBV- or HTLV1-transformed cells through induction of BIC expression. J Virol 85: 8328-8337.

Watabe, M., Hishikawa, K., Takayanagi, A., Shimizu, N., & Nakaki, T. (2004). Caffeic acid phenethyl ester induces apoptosis by inhibition of NFkappaB and activation of Fas in human breast cancer MCF-7 cells. The Journal of Biological Chemistry, 279(7), 6017-26. http://doi.org/10.1074/jbc.M306040200.

Xu D, Zhao L, Del Valle L, Miklossy J, Zhang L (2008) Interferon regulatory factors 4 is involved in Epstein-Barr virus-mediated transformation of human B lymphocytes. J Virol 82: 6251-6258.

Yang Y, Shi J, Tolomelli G, Xu H, Xia J, Wang H. (2013). RARa2 expression confers myeloma stem cell features. Blood, 122: 1437-1447.

Zheng, W., Liu, D., Fan, X., Powers, L., Goswami, M., Hu, Y., . . . Wang, S. A. (2013). Potential therapeutic biomarkers in plasma cell myeloma: a flow cytometry study. Cytometry. Part B, Clinical Cytometry, 84(4), 222-8. http://doi.org/10.1002/cyto.b.21083.

Etzenhouser, B. et al. "Mechanism of Toxicity of Esters of Caffeic and Dihydrocaffeic Acids", Bioorganic & Medicinal Chemistry (2001), 9:199-209.

Beauregard, A-P. et al. "CAPE Analogs Induce Growth Arrest and Apoptosis in Breast Cancer Cells", Molecules (2015), 20:12576-12589.

Koru, O. et al. "Cytotoxic effects of caffeic acid phenethyl ester (CAPE) on the human multiple myeloma cell line", Turk J. Med Sci (2009), 39:863-870.

Akyol et al., "In Vivo and In Vitro Antineopastic Actions of Caffeic Acid Phenethyl Ester (CAPE): Therapeutic Perspectives", Nutrition and Cancer, 2013, vol. 65, No. 4, pp. 515-526, ISSN 0163-5581.

Omene et al., "Propolis and its Active Component, Caffeic Acid Phenethyl Ester (CAPE), Modulate Breast Cancer Therapeutic Targets via an Epigenetically Mediated Mechanism of Action", J. of Cancer Sci Ther, 2013, vol. 5, No. 10, pp. 334-342, ISSN 1948-5956.

Chen Hui-Zhen et al., "Synthesis and antitumor activity of feruloyl and caffeoyl derivatives", Bioorganic & Medical Chemistry Letters, vol. 24. No. 18, Sep. 1, 2014, pp. 4367-4371.

Nagaoka T et al., "Selective antiproliferative activity of caffeic acid phenethyl ester analogues on highly liver-Metastatic murine colon 26-L5 carcinoma cell line", Bioorganic & Medical Chemistry, Elsevier, Amsterdam, NL, vol. 10, No. 10, Jan. 1, 2002, pp. 3351-3359.

Marin, E.H. and Wang, X. Anti-Cancer Effect of Fluorinated Caffeic Acid Phenethyl Ester on Multiple Myeloma Cells. The FASEB Journal, vol. 31, No. 1, Supplement lb533. Apr. 2017.

Jackson et al: "inhibitory effects of caffeic acid phenethyl ester (CAPE) derivatives on multiple myeloma cell growth—Jackson—2019—The FASEB Journal—Wiley Online Library", The Faseb Journal, Apr. 1, 2019, p. 816.13.

Chen J-H et al.: "Inhibitory effect of caffeic acid phenethyle ester on human leukemia HL-60 cells", Cancer Letters, New York, NY, US, vol. 108, No. 2, Jan. 1, 1996, pp. 211-214.

Kurata, A et al: "Enzymatic synthesis of caffeic acid phenethyl ester analogues in ionic liquid", Journal of Biotechnology, Elsevier, Amsterdam NL, vol. 148, No., 2-3.

Qian, Yiping et al: "Structure-activity relationship for anti-haemolysis and cytotoxicity against HL-60 cells of caffeic acid phenethyl ester derivatives", Shengwu Wuli Xuebao (2010), 26(4), 294-300.

Verma R.P. et al. "An approach towards the quantitative structure-activity relationships of caffeic acid and its derivatives", Chembiochem (2004), 5(9), 1188-1195.

Zhu YX, Kortuem KM, Stewart AK. Molecular mechanism of action of immune-modulatory drugs thalidomide, lenalidomide and pomalidomide in multiple myeloma. Leuk Lymphoma. 2013; 54: 683-687.

Boudreau LH, Maillet J, LeBlanc LM, Jean-François J, Touaibia M, et al. (2012) Caffeic Acid Phenethyl Ester and its Amide Analogue are Potent Inhibitors of Leukotriene Biosynthesis in Human Polymorphonuclear Leukocytes. PLoS ONE 7(2): e31833. doi: 10.1371/journal.pone.0031833.

Doiron JA, Leblanc LM, Hebert MJ, Levesque NA, Pare AF, Jean-Francois J, Cormier M, Surette ME, Touaibia M. Structure-activity relationship of caffeic acid phenethyl ester analogs as new 5-lipoxygenase inhibitors. Chem Biol Drug Des. Apr. 2017;89(4):514-528. doi: 10.1111/cbdd. 12874. Epub Nov. 15, 2016. PMID: 27717142.

* cited by examiner

| | KMM-1 | | | MM1.R | | | JJN3 | | |
|---|---|---|---|---|---|---|---|---|---|
| Inhibitor | $IC_{50}$ (uM) | Log $IC_{50}$ | SE Log $IC_{50}$ | $IC_{50}$ (uM) | Log $IC_{50}$ | SE Log $IC_{50}$ | $IC_{50}$ (uM) | Log $IC_{50}$ | SE Log $IC_{50}$ |
| CAPE | 37.5 | 1.6 | 0.05 | 17.8 | 1.3 | 0.1 | 30.0 | 1.5 | 0.1 |
| GL8 | 12.0 | 1.1 | 0.06 | 4.9 | 0.7 | 0.1 | 6.7 | 0.8 | 0.1 |
| As26 | 1.9 | 0.3 | 0.05 | 0.6 | -0.2 | 0.2 | 3.9 | 0.6 | 0.0 |
| J229 | 6.6 | 0.8 | 0.04 | 2.0 | 0.3 | 0.1 | 14.0 | 1.1 | 0.1 |

GL8 $IC_{50}$ = 2.569 J229 $IC_{50}$ = 2.466 LL23 $IC_{50}$ = 2.546

As25 $IC_{50}$ = 2.046 HM7 $IC_{50}$ = 2.296

COMPOSITIONS AND METHODS FOR INHIBITING BLOOD CANCER CELL GROWTH

FIELD

The present disclosure relates to compositions and methods for inhibiting blood cancer cell growth.

BACKGROUND

Every year there are over 30,000 new cases of myeloma, 80,000 new cases of lymphoma, and over 62,000 new cases of leukemia in the US alone. Multiple myeloma is the second most common hematological malignancy and a so far incurable bone marrow cancer. Approximately 1% of all cancers are multiple myeloma (MM) accounting for 2% of all cancer deaths (Kyle et al., 2003; Rajkumar, 2014). The hallmark of multiple myeloma is the transformation of terminally differentiated plasma cells committed to producing polyclonal antibodies into aberrantly proliferating malignant multiple myeloma cells (MMCs) that produce only monoclonal antibodies. This dramatic dysregulation results in disease-related symptoms such as nephropathy and hyperviscosity along with other clinical manifestations such as anemia, extensive skeletal destruction and hypercalcemia (Hengeveld & Kersten, 2015).

The progression from plasma cells to malignant myeloma cells involves multiple genetic events including chromosomal translocations. 50-75% of myeloma patients exhibit chromosome translocations at the immunoglobulin heavy chain (IgH) locus that juxtapose oncogenes from the partner chromosome under the control of strong 3' IgH enhancer elements (Nishida et al., 1997; Turesson et al., 2010; Chesi et al., 1998a). Overexpression of various oncogenes such as FGFR3, MMSET, Cyclin D1, Cyclin D3, cMAF occur depending on the partner locus involved in the translocation (Chesi et al., 1996; Chesi et al.,1998b, Shaughnessy et al., 2001). Elevated expression of OCT2, a key transcription factor involved in IgH translocations has been implicated as a poor prognostic factor and has been associated with reduced survival in MM patients (Toman et al., 2011).

Interferon regulatory factor (IRF4) is an indispensable transcription factor for plasma cell differentiation and deregulation of MUM1/IRF4 by chromosomal translocation in multiple myeloma has been well documented in myeloma patients (Iida et al., 1997). IRF4 has been shown to control plasma cell differentiation and class-switch recombination for creation of functionally competent plasma cells in transgenic mice models (Klein et al., 2006). Overexpression of IRF4 has been linked to poor prognosis in multiple myeloma, especially in certain types of the disease, such as those involving 14q32 translocation (Iida et al., 1997) or Immunoglobulin M (Ryu et al., 2014). IRF4 is constitutively expressed in peripheral T-cell lymphoma (PTCL) cells and drives Myc expression and proliferation. IRF4 promotes proliferation of EBV-transformed cells and deficiency of IRF4 leads to death of cells derived from different hematological malignancies (Xu et al., 2008; Shaffer et al., 2008; Wang et al., 2011). Lymphoma and leukemia are the other common hematological malignancies where high IRF4 protein expression is common in certain subtypes (Wang et al., 2014).Thalidomide is the first of the immunomodulatory (IMiD) class of drug that was found to be effective against multiple myeloma in 1999 (Singhal et al., 1999), while the second generation IMiDs, lenalidomide and pomalidomide demonstrated more potent anti-myeloma, anti-inflammatory and immunomodulatory activities (Marriot et al., 2001). The biochemical mechanism underlying the therapeutic activity of IMiDs was poorly understood until recently when thalidomide was shown to bind to the protein cereblon (CRBN), which is the substrate-recognition component of a cullin-dependent E3 ubiquitin ligase, inhibiting its auto-ubiquitination activity (Ito et al., 2010, Zhu et al. 2013). Loss of IKZF1 (ikaros) and IKZF3 (aiolos) by lenalidomide treatment in lenalidomide sensitive myeloma cell lines was followed by a decrease in IRF4, acting downstream of IKZF1 and/or IKZF3 (Ito et al., 2010), thus leading to a toxic outcome for multiple myeloma cells.

The genetic heterogeneity of myeloma poses a great challenge for treatment of the disease. Also, high IRF4 levels have recently been identified as the potential mechanism of resistance to IMiDs, lenalidomide and pomalidomide in Waldenström's macroglobulinemia, a type of lymphoma/blood cancer (Bertrand et al., 2017). Current chemotherapeutics exhibit several adverse side effects that affect the quality of life of blood cancer patients, as well as face they face the challenge of resistance by blood cancer cells. This warrants the need for novel therapeutics for multiple myeloma and other blood cancers with elevated IRF4 protein expression. In the search for novel cancer cells. This warrants the need for novel therapeutics for multiple myeloma and other blood cancers with elevated IRF4 protein expression. In the search for novel compounds for cancer treatment, natural products affecting cell survival and cancer cell death pathways have gained the interest of the scientific community (Natarajan et al.,1996; Watabe et al., 2004; Wang et al., 2010; Szliszka et al., 2011).

Caffeic acid (3,4-dihydroxycinnamic acid) phenethyl ester (CAPE) having the structure

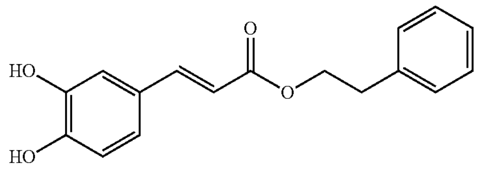

CAPE is an active principle of propolis from honeybee hives and a structural analogue of flavonoids. It has been known to exhibit diverse biological potential such as anti-oxidant (Okutan & Uz, 2005), immunomodulatory (Larki-Harchegani et al., 2013; Sy et al 2011), anti-inflammatory (Armutcu & Turan, 2015), anti-viral (Fesen et al., 1994; Shen et al., 2013) and anti-tumor activities (Onori et al., 2009; Patel S., 2016). Analogs of CAPE have been extensively investigated for their anti-inflammatory property (Sanderson et al., 2013) through inhibition of 5-hydroxy lipoxygenase (Doiron et al., 2017).

SUMMARY OF THE DISCLOSURE

The present invention in certain embodiments relates to methods for inhibiting the growth of blood cancer cells comprising contacting the cells with a caffeic acid phenpropyl ester (GL8) analogue selected from the group consisting of As26, J229, J91, LL27, LL23, HM7, As25, MT26, and J205, with their structural formulae depicted in Table 1, or a pharmaceutically acceptable salt thereof, in an amount effective to inhibit the growth. In one embodiment, the blood cancer cells are myeloma cells. In a further embodiment, the myeloma cells are immune-modulatory drug (IMiD) resistant. In a still further embodiment, the myeloma cells are lenalidomide resistant myeloma cells. In another embodiment, the blood cancer cells The present invention in certain other embodiments relates to methods for inhibiting the growth of blood cancer cells in a patient including administering to a patient a therapeutically effective amount of a caffeic acid phenpropyl ester (GL8) analogue selected from the group consisting of As26, J229, J91, LL27, LL23, HM7, As25, MT26 and J205, with their structural formulae depicted in Table 1, or a pharmaceutically acceptable salt thereof.

In one embodiment, the blood cancer cells are myeloma cells. In a further embodiment, the myeloma cells are immunomodulatory drug (IMiD) resistant. In a still further embodiment, the myeloma cells are lenalidomide-resistant myeloma cells. In another embodiment, the blood cancer cells are lymphoma cells. In a still further embodiment, the lymphoma cells are lenalidomide-resistant lymphoma cells. In another embodiment, the blood cancer cells are leukemia cells.

In another embodiment, a GL8 analogue selected from the group consisting of As26, J229, J91, LL27, LL23, HM7, As25, MT26 and J205, is used in conjunction with an IMiD to treat a patient.

The present invention in certain other embodiments relates to compositions for inhibiting the growth of blood cancer cells including a therapeutically effective amount of a caffeic acid phenpropyl ester (GL8) analogue selected from the group consisting of As26, J229, J91, LL27, LL23, HM7, As25, MT26 and J205, with their structural formulae depicted in Table 1, or a pharmaceutically acceptable salt thereof.

In one embodiment, the blood cancer cells are myeloma cells. In a further embodiment, the myeloma cells are immunomodulatory drug (IMiD) resistant. In a still further embodiment, the myeloma cells are lenalidomide resistant myeloma cells. In another embodiment, the blood cancer cells are lymphoma cells. In another embodiment, the blood cancer cells are leukemia cells. In certain embodiments, the composition is a pharmaceutical composition. In certain embodiments, the composition is a dietary supplement. In certain embodiments, the composition includes a carrier. In certain other embodiments, the carrier is a pharmaceutically acceptable carrier.

The present invention in certain embodiments relates to the use of a caffeic phenpropyl ester (GL8) analogue selected from the group consisting of As26, J229, J91, LL27, LL23, HM7, As25, MT26 and J205 with their structural formulae depicted in Table 1, or a pharmaceutically acceptable salt thereof, for inhibiting the growth of blood cancer cells. In one embodiment, the blood cancer cells are myeloma cells. In a further embodiment, the myeloma cells are immunomodulatory drug (IMiD) resistant. In a still further embodiment, the myeloma cells are lenalidomide resistant myeloma cells. In another embodiment, the blood cancer cells are lymphoma cells. In another embodiment, the blood cancer cells are leukemia cells.

The present invention in certain embodiments relates a method of decreasing a cereblon pathway protein in a patient including administering to the patient a therapeutically effective amount of a caffeic acid phenpropyl ester (GL8) analogue selected from the group consisting of As26, J229, J91, LL27, LL23, HM7, As25, MT26 and J205, with their structural formulae depicted in Table 1, or a pharmaceutically acceptable salt thereof, whereby blood cancer cell growth is inhibited. In one embodiment, the cereblon pathway protein is Ikaros. In another embodiment, cereblon pathway protein is IRF4.

The present invention in certain other embodiments relates to compositions for decreasing a cereblon pathway protein including a therapeutically effective amount of a caffeic acid phenpropyl ester (GL8) analogue selected from the group consisting of As26, J229, J91, LL27, LL23, HM7, As25, MT26 and J205, with their structural formulae depicted in Table 1, or a pharmaceutically acceptable salt thereof. In one embodiment, the cereblon pathway protein is Ikaros. In another embodiment, cereblon pathway protein is IRF4.

The present invention in certain embodiments relates the use of a caffeic phenpropyl ester (GL8) analogue selected from the group consisting of As26, J229, J91, LL27, LL23, HM7, As25, MT26 and J205, with their structural formulae depicted in Table 1, or a pharmaceutically acceptable salt thereof.

The present invention in certain embodiments relates to methods for inhibiting the growth of blood cancer cells including contacting the cells with a caffeic acid phenpropyl ester (GL8) analogue selected from the group consisting of As26, J229, J91, LL27, LL23, HM7, As25, MT26 and J205, with their structural formulae depicted in Table 1, or a pharmaceutically acceptable salt thereof, in an amount effective to inhibit the growth. In one embodiment, the blood cancer cells are myeloma cells. In a further embodiment, the myeloma cells are immunomodulatory drug (IMiD) resistant. In a still further embodiment, the myeloma cells are lenalidomide resistant myeloma cells. In another embodiment, the blood cancer cells are lymphoma cells. In another embodiment, the blood cancer cells are leukemia cells.

The present invention in certain embodiments relates to methods for inhibiting the growth of blood cancer cells including contacting the cells with a caffeic acid phenpropyl ester (GL8) analogue selected from the group consisting of As26, J229, J91, LL27, LL23, and HM7 exhibiting remarkable anti-myeloma activity; in other embodiments, the analogue group consisting of As26, HM7, As25, MT26 and J229 exhibiting superior anti-lymphoma activity and in still further embodiments, the analogue group consisting of As26, J205, J229, LL27 and LL23 with remarkable anti-leukemia activity, with their structural formulae depicted in Table 1, or a pharmaceutically acceptable salt thereof, in an amount effective to inhibit the growth. In one embodiment, the blood cancer cells are myeloma cells. In a further embodiment, the myeloma cells are immunomodulatory drug (IMiD) resistant. In a still further embodiment, the myeloma cells are lenalidomide resistant myeloma cells. In another embodiment, the blood cancer cells are lymphoma cells. In another embodiment, the blood cancer cells are leukemia cells.

In certain aspects of the present invention, pharmaceutically acceptable compositions are provided, wherein these compositions comprise any of the compounds or a pharmaceutically acceptable salt thereof, as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative or a prodrug thereof. According to the present invention, a pharmaceutically acceptable derivative or a prodrug includes, but is not limited to, pharmaceutically acceptable salts, esters, salts of such esters, or any other adduct or derivative which upon administration to a patient in need thereof is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

DETAILED DESCRIPTION

Figure 1:
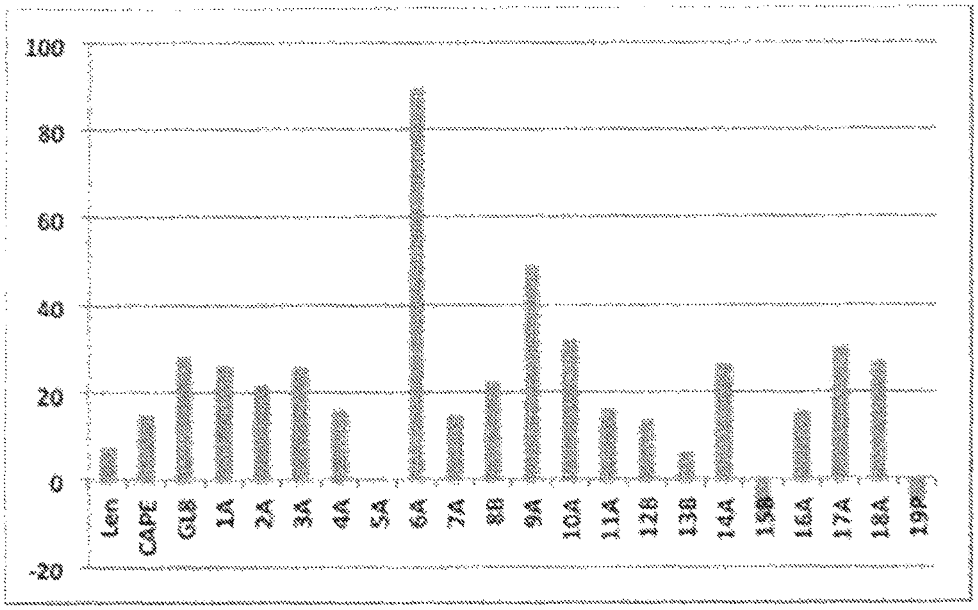
FIG. 1 is a bar graph depicting cell growth inhibitory effect of caffeic acid phenpropyl ester (GL8) analogues according to certain aspects of the present disclosure at 10 uM concentration on IMiD-resistant human myeloma cells (KMM1)

In certain embodiments of the present invention, a systematic molecules design strategy was used to obtain 18 analogues of GL8/caffeic acid phenpropyl ester, which are set out in Table 1.

TABLE 1

| Molecule Code (Used in Anti-blood Cancer Bioactivity Evaluation Experiments) | Molecule | | Chemical Name |
|---|---|---|---|
| 18A | LL23 | 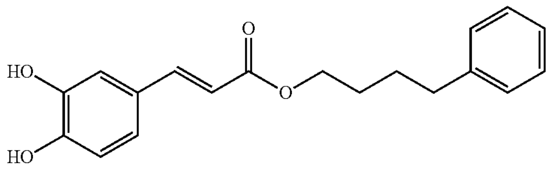 [SMILES: O=C(/C=C/c1ccc(O)c(O)c1)OCCCCc1ccccc1] | (E)-4-phenylbutyl 3-(3,4-dihydroxyphenyl)acrylate |
| 17A | LL27 | 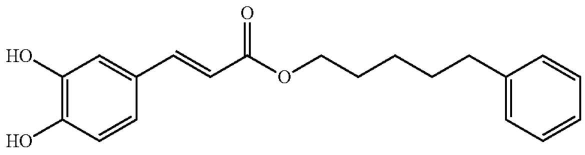 [SMILES: O=C(/C=C/c1ccc(O)c(O)c1)OCCCCCc1ccccc1] | (E)-4-phenylbutyl 3-(3,4-dihydroxyphenyl)acrylate |

TABLE 1-continued

| Molecule Code (Used in Anti-blood Cancer Bioactivity Evaluation Experiments) | Molecule | | Chemical Name |
| --- | --- | --- | --- |
| 16A | LL28 | 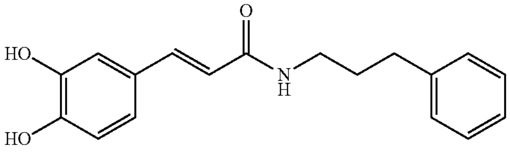 [SMILES: O=C(/C=C/c1ccc(O)c(O)c1)NCCCc1ccccc1] | (E)-3-(3,4-dihydroxyphenyl)-N-(3-phenylpropyl)acrylamide |
| 15B | HM5 | 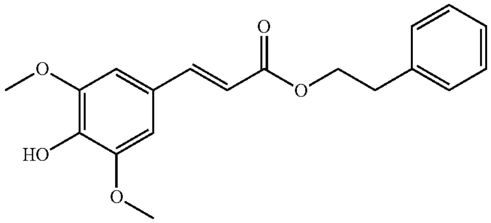 [SMILES: COc1cc(/C=C/C(=O)OCCc2ccccc2)cc(OC)c1O] | (E)-phenethyl 3-(4-hydroxy-3,5-dimethoxyphenyl)acrylate |
| 14A | HM7 | 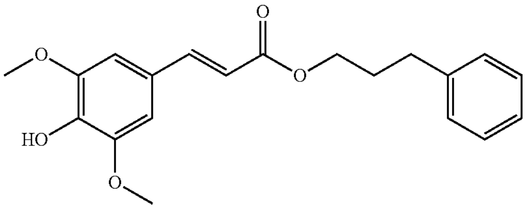 [SMILES: COc1cc(/C=C/C(=O)OCCCc2ccccc2)cc(OC)c1O] | (E)-3-phenylpropyl 3-(4-hydroxy-3,5-dimethoxyphenyl)acrylate |
| 13B | MT49 | 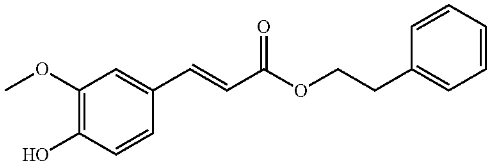 [SMILES: COc1cc(/C=C/C(=O)OCCc2ccccc2)ccc1O] | (E)-phenethyl 3-(4-hydroxy-3-methoxyphenyl)acrylate |
| 12B | MT50 | 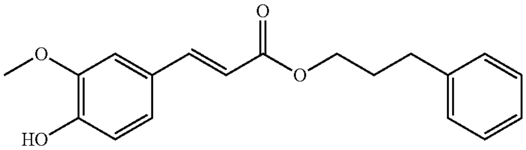 [SMILES: COc1cc(/C=C/C(=O)OCCCc2ccccc2)ccc1O] | (E)-3-phenylpropyl 3-(4-hydroxy-3-methoxyphenyl)acrylate |
| 11A | LL14 | 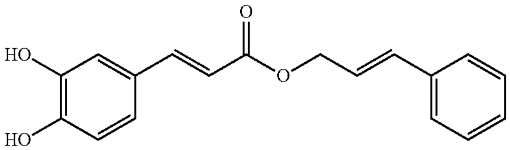 [SMILES: O=C(/C=C/c1ccc(O)c(O)c1)OC/C=C/c1ccccc1] | (2E)-cinnamyl 3-(3,4-dihydroxyphenyl)acrylate |
| 10A | J91 | 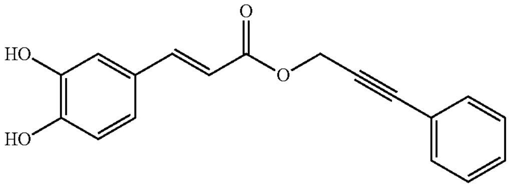 [SMILES: O=C(/C=C/c1ccc(O)c(O)c1)OCC#Cc1ccccc1] | (E)-3-phenylprop-2-ynyl 3-(3,4-dihydroxyphenyl)acrylate |
| 9A | J229 | 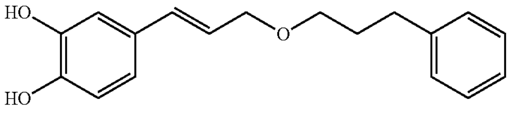 [SMILES: Oc1ccc(/C=C/COCCCc2ccccc2)cc1O] | 4-((E)-3-(3-phenylpropoxy)prop-1-enyl)benzene-1,2-diol |

TABLE 1-continued

| Molecule Code (Used in Anti-blood Cancer Bioactivity Evaluation Experiments) | Molecule | | Chemical Name |
|---|---|---|---|
| 8B | J205 | 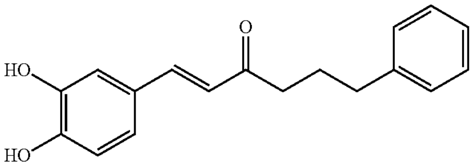 [SMILES: O=C(/C=C/c1ccc(O)c(O)c1)CCCc1ccccc1] | (E)-1-(3,4-dihydroxyphenyl)-6-phenylhex-1-en-3-one |
| 7A | As25 | 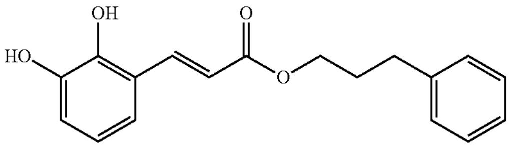 [SMILES: O=C(/C=C/c1cccc(O)c1O)OCCCc1ccccc1] | (E)-3-phenylpropyl 3-(2,3-dihydroxyphenyl)acrylate |
| 6A | As26 | 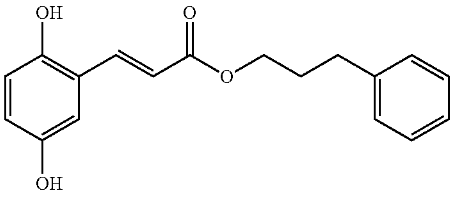 [SMILES: O=C(/C=C/c1cc(O)ccc1O)OCCCc1ccccc1] | (E)-3-phenylpropyl 3-(2,5-dihydroxyphenyl)acrylate |
| 5A | MT72 | 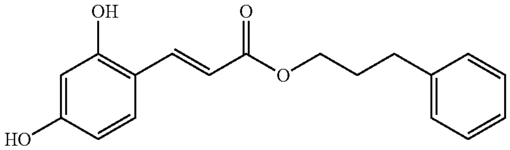 [SMILES: O=C(/C=C/c1ccc(O)cc1O)OCCCc1ccccc1] | (E)-3-phenylpropyl 3-(2,4-dihydroxyphenyl)acrylate |
| 4A | GL7 | 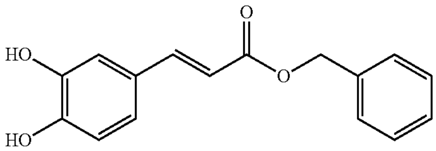 [SMILES: O=C(/C=C/c1ccc(O)c(O)c1)OCc1ccccc1] | (E)-benzyl 3-(3,4-dihydroxyphenyl)acrylate |
| 3A | GL9 | 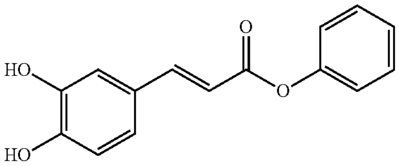 [SMILES: O=C(/C=C/c1ccc(O)c(O)c1)Oc1ccccc1] | (E)-phenyl 3-(3,4-dihydroxyphenyl)acrylate |
| 2A | MT25 | 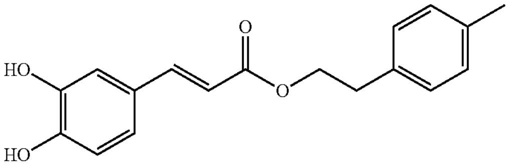 [SMILES: Cc1ccc(CCOC(=O)/C=C/c2ccc(O)c(O)c2)cc1] | (E)-(4-methylphenethyl) 3-(3,4-dihydroxyphenyl)acrylate |
| 1A | MT26 | 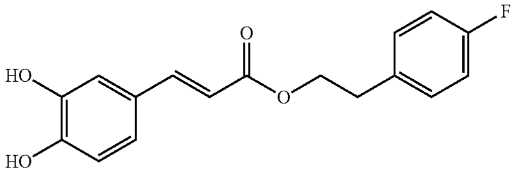 [SMILES: O=C(/C=C/c1ccc(O)c(O)c1)OCCc1ccc(F)cc1] | (E)-(4-fluorophenethyl) 3-(3,4-dihydroxyphenyl)acrylate |

In certain embodiments of the present invention, the molecule design strategy used to obtain the 18 analogues of Table 1 is set out in Scheme 1.

Scheme 1

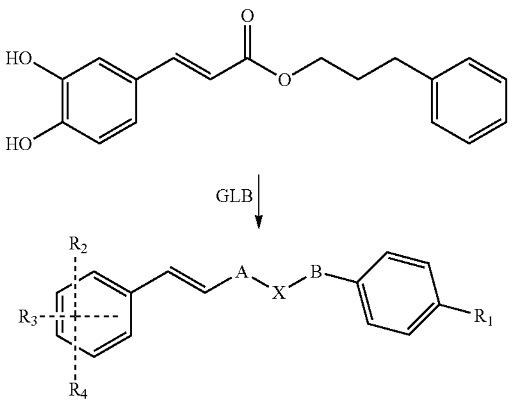

A = $CH_2$, C=O
B = a bond; $CH_2$; $(CH_2)n$: n = 1-5; alkene; alkyne
X = O, NH, CH2
R1 = $CH_3$, F
$R_2$ = H, OH, $OCH_3$
$R_3$ = H, OH, $OCH_3$
$R_4$ = H, OH, $OCH_3$ In certain embodiments of the present invention, a bioactivity evaluation was then carried out to evaluate the anti-blood cancer activity of the 18 analogues in Table 1 in comparison to the standard drug, lenalidomide, parent compounds CAPE, GL8 and propolis. In certain embodiments of the present invention, the bioactivity of the 18 analogs of Table 1 in human myeloma, lymphoma and leukemia cell lines was evaluated and analogues with superior anti-myeloma, anti-lymphoma and anti-leukemia activity were identified.

In certain embodiments of the present invention, the remarkable cancer cell growth inhibitory potential of caffeic acid phenpropyl ester analogues was established by treating human leukemia, myeloma and lymphoma cell lines with the analogues of Table 1 and measuring the viability of blood cancer cells by cell viability assay. The efficacy of the analogues of Table 1 in comparison to a standard chemotherapy drug was confirmed.

With reference to Table 1, Table 2 and FIG. 1, FIG. 1 is a bar graph depicting cell growth inhibitory effect of caffeic acid phenpropyl ester (GL8) analogues at 10 uM concentration according to certain aspects of the present disclosure on human myeloma cells (Cell line: KMM-1; 48 hr treatment). Caffeic acid phenpropyl ester (GL8) analogues that exhibit superior anti-myeloma cell growth inhibition, in decreasing order of bioactivity at 10 uM concentration, are As26, J229, J91, LL27, LL23 and HM7.

TABLE 2

| Molecule Code/ Bioactivity Assay Treatment Condition | Molecule | Growth Inhibition (%) |
|---|---|---|
| Len | Lenalidomide | 7.5 |
| CAPE | CAPE | 14.7 |
| GL8 | GL8 | 28.2 |

TABLE 2-continued

| Molecule Code/ Bioactivity Assay Treatment Condition | Molecule | Growth Inhibition (%) |
|---|---|---|
| 1A | MT26 | 25.9 |
| 2A | MT25 | 21.6 |
| 3A | GL9 | 26 |
| 4A | GL7 | 15.9 |
| 5A | MT72 | −0.2 |
| 6A | As26 | 89.7 |
| 7A | As25 | 15.1 |
| 8B | J205 | 22.2 |
| 9A | J229 | 49.4 |
| 10A | J91 | 31.7 |
| 11A | LL14 | 16.1 |
| 12B | MT50 | 13.6 |
| 13B | MT49 | 6.5 |
| 14A | HM7 | 26.6 |
| 15B | HM5 | −8.6 |
| 16A | LL28 | 15.8 |
| 17A | LL27 | 30.5 |
| 18A | LL23 | 27.2 |
| 19P | Propolis | −5.2 |

Figure 2:
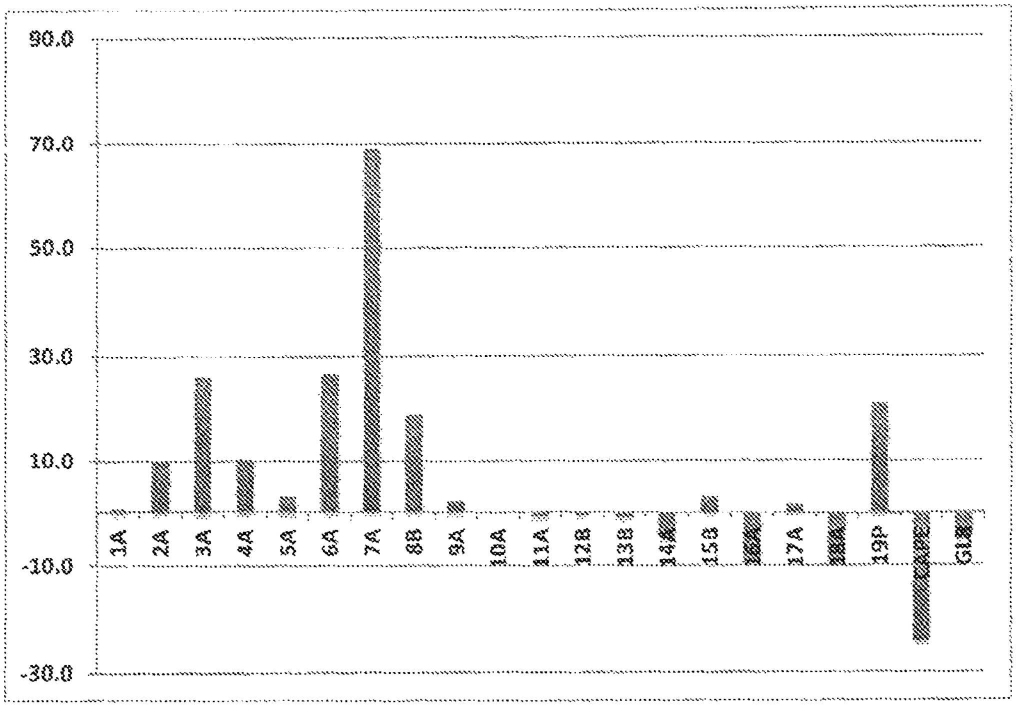
FIG. 2 is a bar graph depicting cell growth inhibitory effect of caffeic acid phenpropyl ester (GL8) analogues at 1 uM concentration according to certain aspects of the present disclosure on human lymphoma cells (IMiD-resistant cell line—OCI-Ly3)

With reference to Table 3 and FIG. 2, FIG. 2 is a bar graph depicting cell growth inhibitory effect of caffeic acid phenpropyl ester (GL8) analogues according to certain aspects of the present disclosure at 1 uM concentration on human lymphoma cells (Cell line: OCI-LY3; 48 hr treatment).

TABLE 3

| Molecule Code/ Bioactivity Assay Treatment Condition | Molecule | Growth Inhibition (%) |
|---|---|---|
| 1A | MT26 | 0.7 |
| 2A | MT25 | 10.0 |
| 3A | GL9 | 26.3 |
| 4A | GL7 | 10.5 |
| 5A | MT72 | 3.3 |
| 6A | As26 | 26.6 |
| 7A | As25 | 69.0 |
| 8B | J205 | 18.7 |
| 9A | J229 | 2.3 |
| 10A | J91 | 0.3 |
| 11A | LL14 | −1 |
| 12B | MTSO | −0.7 |
| 13B | MT49 | −1.0 |
| 14A | HM7 | −4.9 |
| 15B | HM5 | 3.1 |
| 16A | LL28 | −9.5 |
| 17A | LL27 | 1.6 |
| 18A | LL23 | −9.3 |
| 19P | Propolis | 20.7 |
| CAPE | CAPE | −24.3 |
| GL8 | GL8 | −4.6 |

Figure 3:
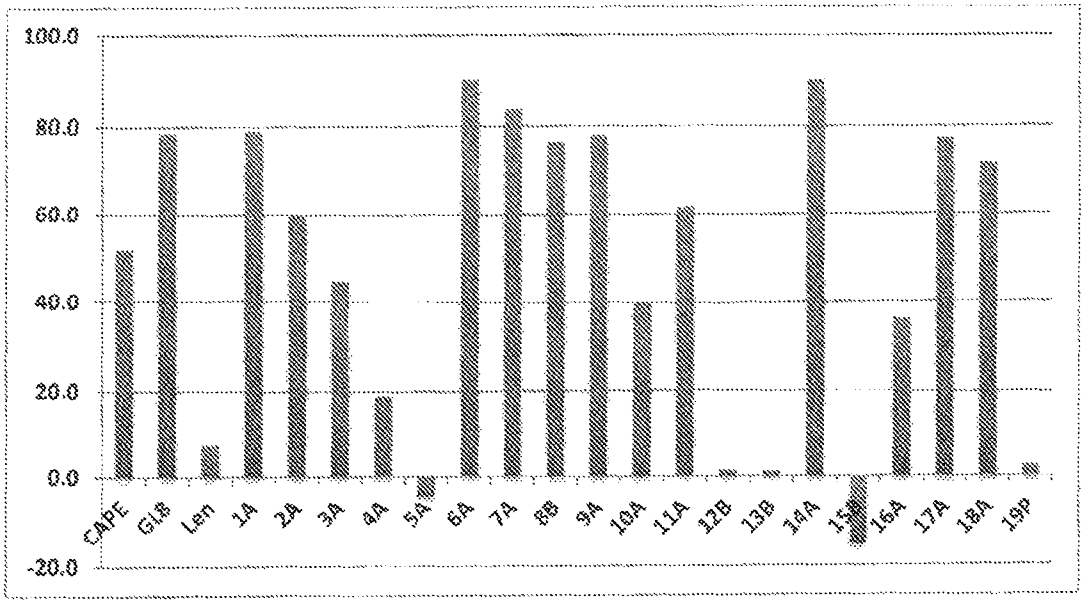
FIG. 3 is a bar graph depicting cell growth inhibitory effect of caffeic acid phenpropyl ester (GL8) analogues at 10 uM concentration according to certain aspects of the present disclosure on human lymphoma cells (IMiD-resistant cell line—OCI-Ly3)

With reference to Table 1, Table 4 and FIG. 3, FIG. 3 is a bar graph depicting cell growth inhibitory effect of caffeic acid phenpropyl ester (GL8) analogues according to certain aspects of the present disclosure at 10 uM concentration on human lymphoma cells (Cell line: OCI-LY3; 48 hr treatment). Caffeic acid phenpropyl ester analogues according to certain aspects of the present disclosure that exhibited superior anti-lymphoma cell growth inhibition, in decreasing order of bioactivity at 10 uM concentration, are As26, HM7, As25, MT26 and J229.

TABLE 4

| Molecule Code/ Bioactivity Assay Treatment Condition | Molecule | Growth Inhibition (%) |
|---|---|---|
| CAPE | CAPE | 51.8 |
| GL8 | GL8 | 78.7 |
| Len | Lenalidomide | 7.5 |
| 1A | MT26 | 79.3 |
| 2A | MT25 | 59.8 |
| 3A | GL9 | 44.7 |
| 4A | GL7 | 18.9 |
| 5A | MT72 | −4.5 |
| 6A | As26 | 90.3 |
| 7A | As25 | 84.0 |
| 8B | J205 | 76.6 |
| 9A | J229 | 78.2 |
| 10A | J91 | 39.8 |
| 11A | LL14 | 61.5 |
| 12B | MT50 | 1.5 |
| 13B | MT49 | 1.2 |
| 14A | HM7 | 90.0 |
| 15B | HM5 | −15.4 |
| 16A | LL28 | 36.0 |
| 17A | LL27 | 77.4 |
| 18A | LL23 | 71.7 |
| 19P | Propolis | 3.1 |

Figure 4:
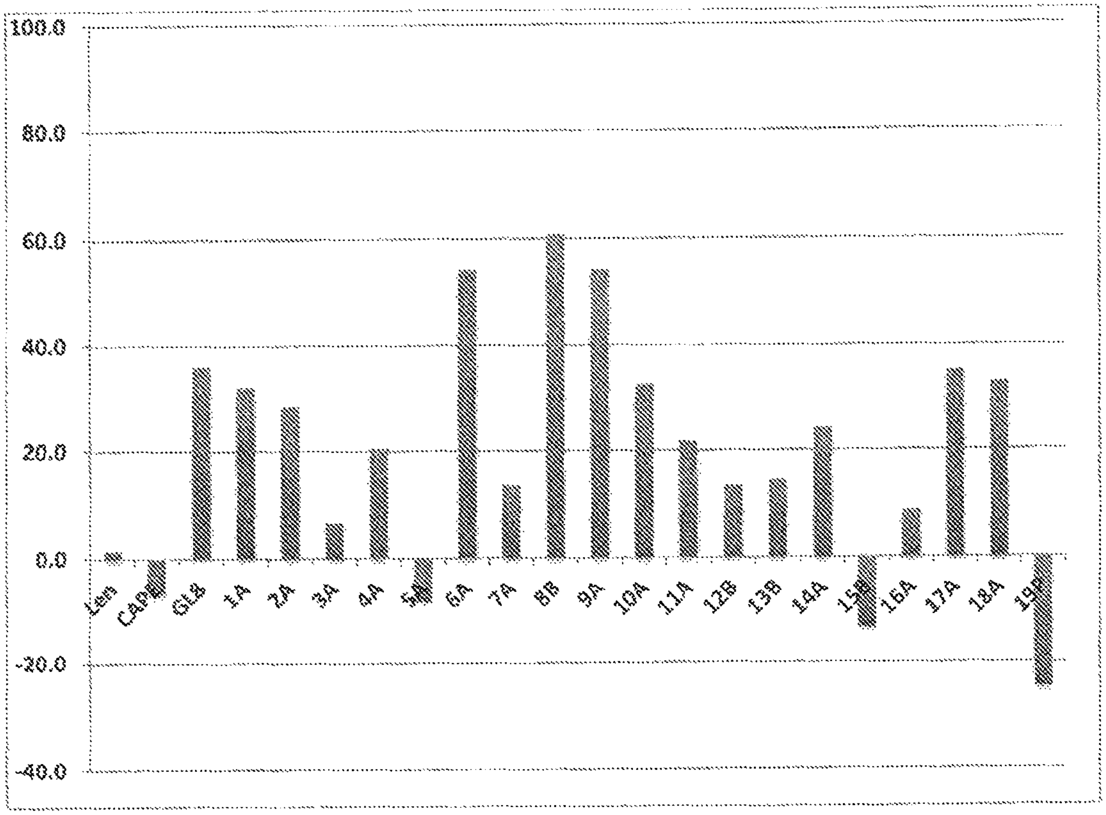
FIG. 4 is a bar graph depicting cell growth inhibitory effect of caffeic acid phenpropyl ester (GL8) analogues at 10 uM concentration according to certain aspects of the present disclosure on human leukemia cells.

With reference to Table 5 and FIG. 4, FIG. 4 is a bar graph depicting cell growth inhibitory effect of caffeic acid phenpropyl ester (GL8) analogues at 10 uM concentration according to certain aspects of the present disclosure on human leukemia cells (Cell line: HL-60; 48 hr treatment).

TABLE 5

| Molecule Code/ Bioactivity Assay Treatment Condition | Molecule | Growth Inhibition (%) |
|---|---|---|
| Len | Lenalidomide | 1.6 |
| CAPE | CAPE | −6.8 |
| GL8 | GL8 | 36.0 |
| 1A | M126 | 32.1 |
| 2A | M125 | 28.7 |
| 3A | GL9 | 6.8 |
| 4A | GL7 | 20.5 |
| 5A | M172 | −8.2 |
| 6A | As26 | 54.4 |
| 7A | As25 | 13.6 |
| 8B | J205 | 60.7 |
| 9A | J229 | 54.3 |
| 10A | J91 | 32.4 |
| 11A | LL14 | 21.6 |
| 12B | MT50 | 13.4 |
| 13B | M149 | 14.4 |
| 14A | HM7 | 24.1 |
| 15B | HM5 | −13.3 |
| 16A | LL28 | 8.7 |
| 17A | LL27 | 35.2 |
| 18A | LL23 | 33.0 |
| 19P | Propolis | −24.9 |

In certain embodiments, the As26, J229, J91, LL27, LL23, HM7, As25, MT26, and J205 analogues decrease the levels of several key proteins in cereblon pathway including the protein, IRF4. In certain embodiments, the analogues of Table 1 decrease the levels of several key genes in cereblon pathway including the gene, IRF4. In certain embodiments, the analogues of Table 1 decrease the levels of several key proteins in cereblon pathway including the protein, Ikaros. In certain embodiments, the analogues of Table 1 decrease the levels of several key genes in cereblon pathway including the gene, Ikaros. In certain embodiments, the analogues of Table 1 exhibit remarkable cell growth inhibitory activity on myeloma and lymphoma cell lines that are non-responsive to lenalidomide. In other embodiments of the present invention, analogues, other than the 18 analogues of Table 1, derived using Scheme 1 may also be used in the present invention.

Figure 5A:
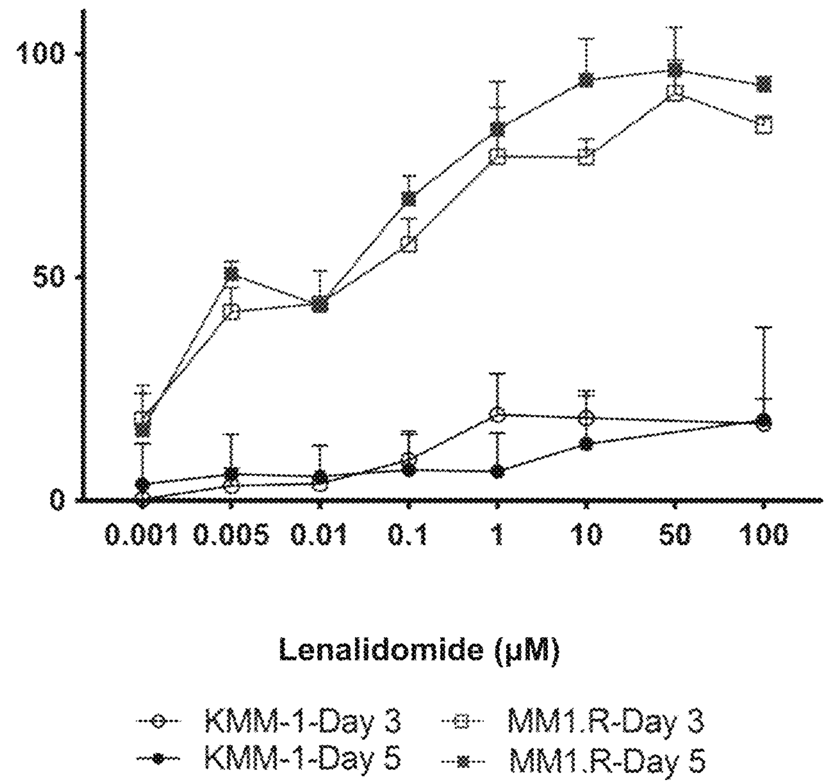
FIG. 5A is a graph showing the inhibition of myeloma cell lines treated with various concentrations of lenalidomide.
Figure 5B:
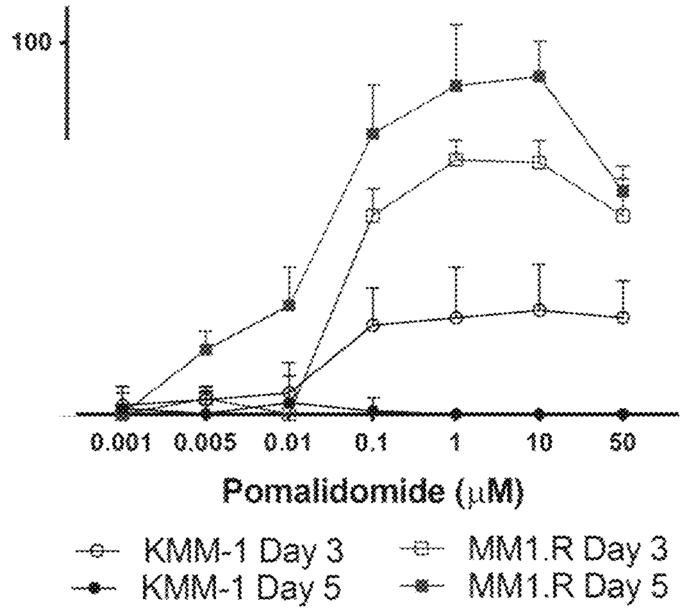
FIG. 5B is a graph showing the inhibition of myeloma cell lines treated with various concentrations of pomalidomide.
Figures 5C, 5D:
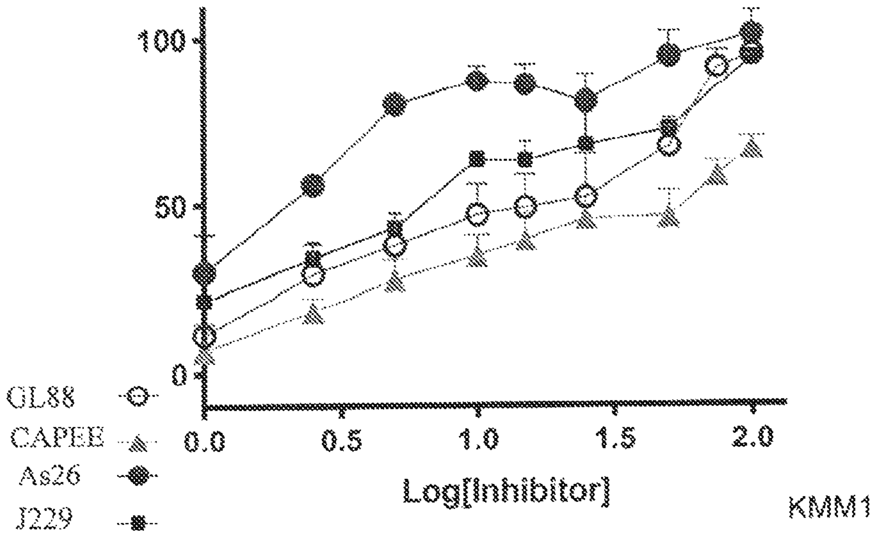
FIG. 5C is a table of ICso values of CAPE, GL8, As26 and J229 tested on both IMiD-sensitive (MMIR) and IMID-resistant human myeloma cells (KMM1 and JJN3)
FIG. 5D is a graph showing the inhibition of KMM1 cells (lenalidomide-resistant) treated with various concentrations of CAPE, GL8, As26 and J229;. 5E is a graph showing the inhibition of MM1R cells (lenalidomide-sensitive) treated with various concentrations of CAPE, GL8, As26 and J229.
Figure 5E:
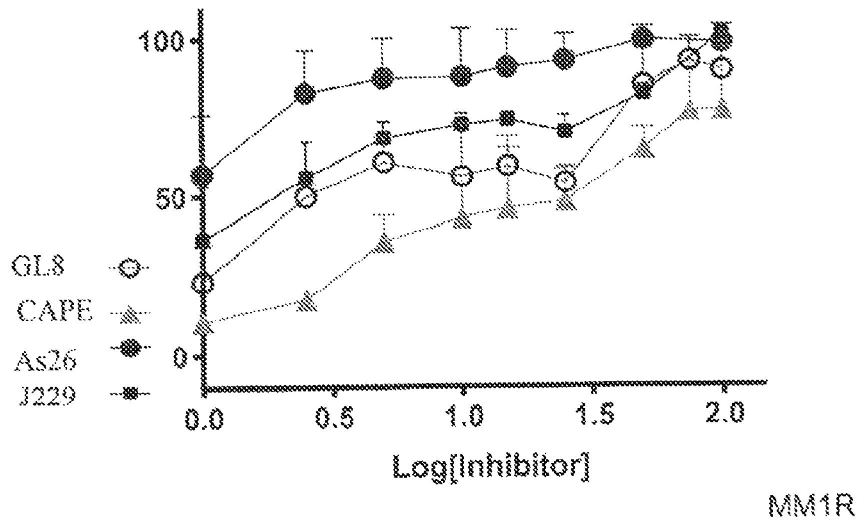
FIG. 5F is a graph showing the inhibition of JJN3 cells (lenalidomide-resistant) treated with various concentrations of CAPE, GL8, As26 and J229.
Figure 5F:
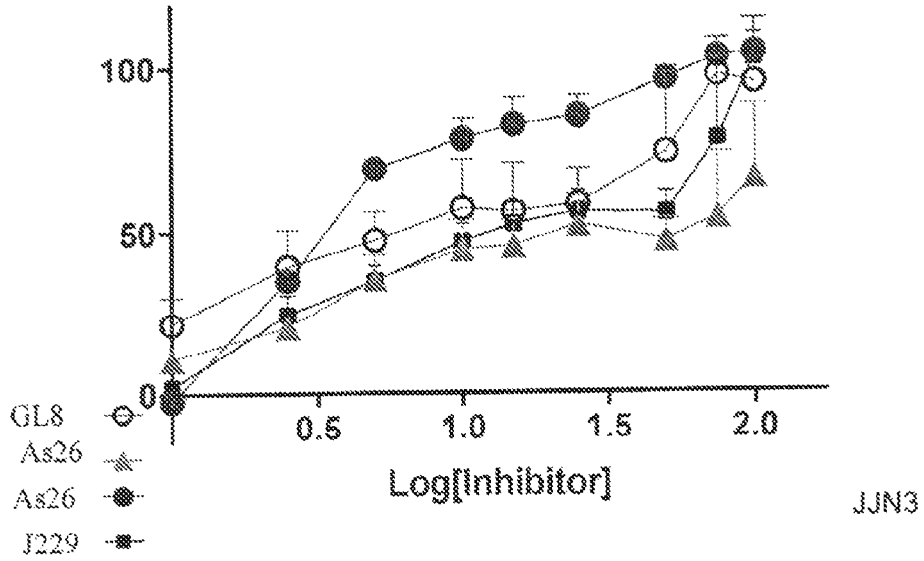

Referring to FIG. 5A to FIG. 5F, As26 exhibited superior myeloma cell growth inhibitory effect in comparison to IMiDs, CAPE, and analogs GL8 and J229. Myeloma cell lines were treated for 3 or 5 days with increasing concentration of lenalidomide (FIG. 5A) and pomalidomide (FIG. 5B). KMM1 cells (FIG. 5D), MM1R cells (FIG. 5E), and JJN3 cells (FIG. 5F) were treated for 48 hours with varying concentration of CAPE, GL8, As26 and J229. The cell growth inhibition was determined by PrestoBlue cell viability assay. Data from three independent experiments is presented as mean±SD. IC50 values (FIG. 5C) representing half-maximal inhibitory concentration of compounds were determined using GraphPad prism analyses software.

Induction of apoptosis in myeloma cells by various inhibitors was determined by staining exposed phosphatidylserine with Annexin V-FITC and DNA with Propidium iodide using Alexa Fluor® 488 annexin V/Dead Cell Apoptosis Kit (Invitrogen, ThermoFisher Scientific, CA) according to the manufacturer's instructions. Single-cell suspensions were analyzed on a Beckmann Coulter Gallios Flow Cytometer with Kaluza analyses software. Twenty-five thousand events were acquired for every condition. Apoptotic cells were scored as Annexin V+, PI− and Annexin V+, PI+.

Figure 6:
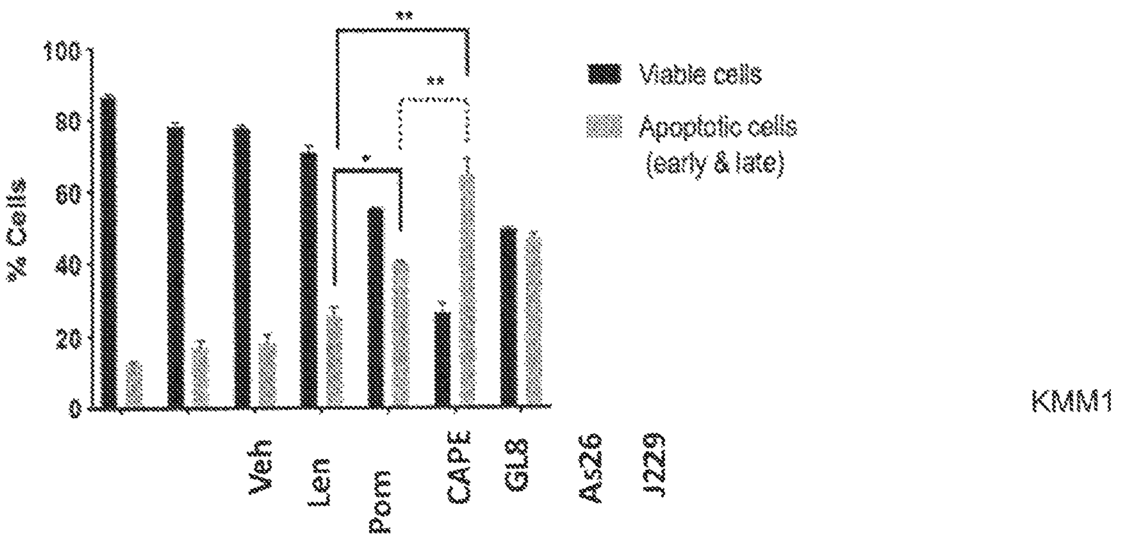
FIG. 6 is a graph showing the apoptotic effect on KMM1 myeloma cells treated with veh/vehicle (DMSO), lenalidomide, pomalidomide, CAPE, GL8, As26 and J229.

Referring to FIG. 6, Apoptotic effect of veh/vehicle (DMSO), lenalidomide (len), pomalidomide (pom), CAPE, GL8, As26 and J229 (all compounds at 10 uM concentration) on KMM1 cells upon 72-hour treatment followed by Annexin V-PI flow cytometry analyses is shown. Percentage of early and late apoptotic cells are presented as mean±SD (*P≤0.05; **P≤0.01). Remarkable apoptotic effect by As26 can be observed.

Figure 7A:
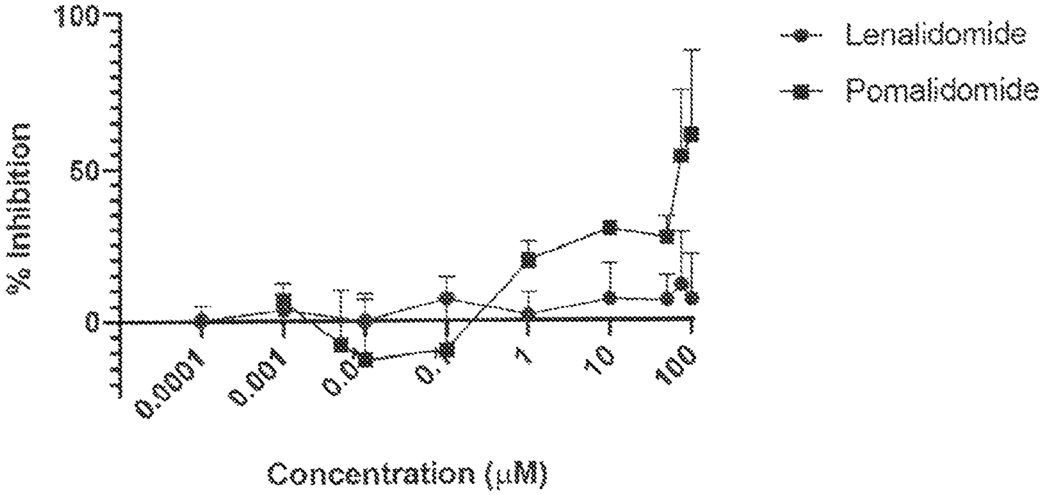
FIG. 7A is a graph showing lymphoma cell growth inhibitory effect in comparison to a 3-day treatment of IMiDs.
Figure 7B:
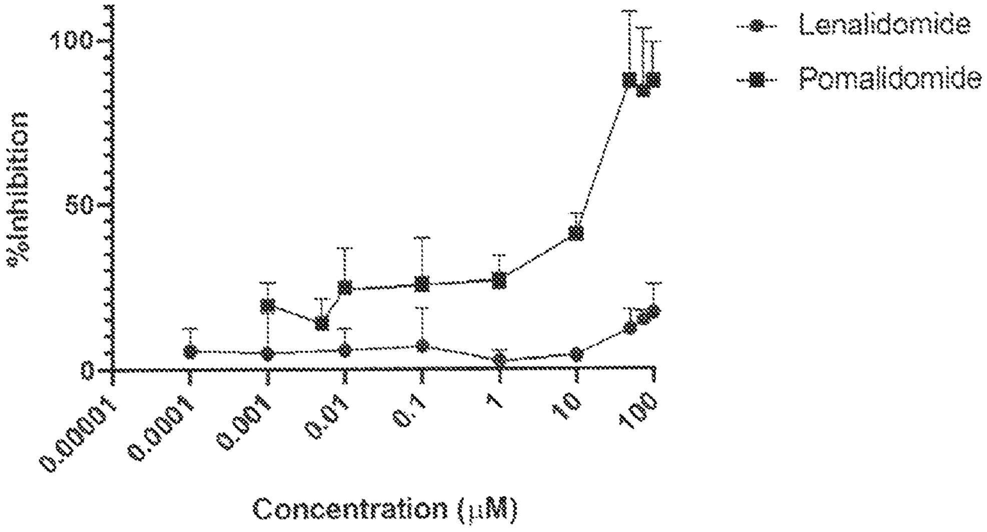
FIG. 7B is a graph showing lymphoma cell growth inhibitory effect in comparison to 5-day treatment of IMiDs.
Figure 7C:
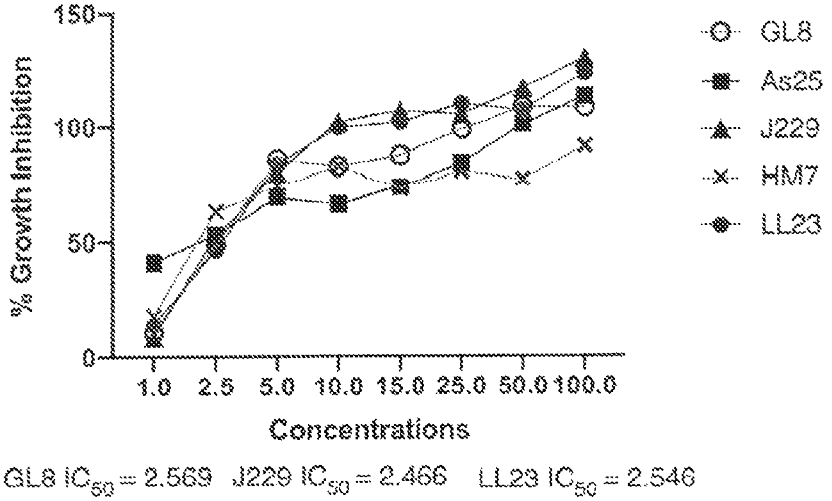
FIG. 7C is a graph showing lymphoma cell growth inhibitory effect in comparison to a 2-day treatment with GL8, As25, J229, HM7, and LL23.

Referring to FIGS. 7A to FIG. 7C, lymphoma cell growth inhibitory effect in comparison to 3-day treatment of IMiDs (FIG. 7A), 5-day treatment of IMiDs (FIG. 7B) and 2-day or 48 hr treatment of GL8, J229, LL23, As25 and HM7 on U2932 Lymphoma cell line determined by PrestoBlue cell viability assays (FIG. 7C).

Figure 8:
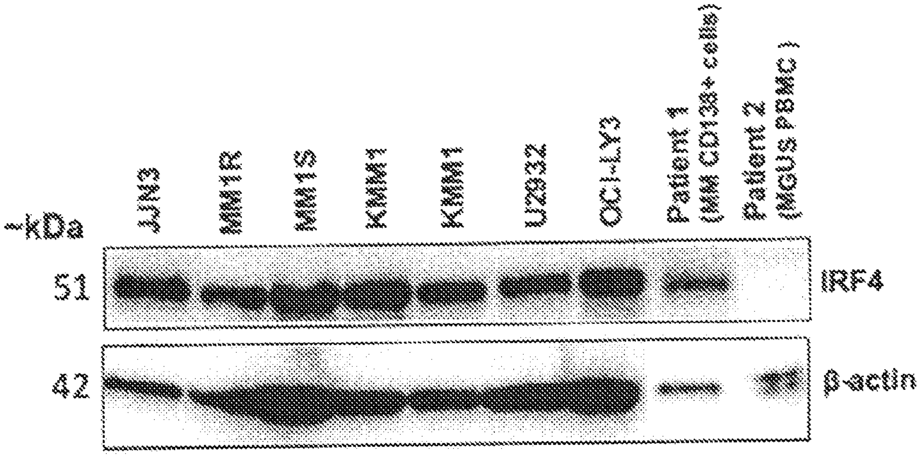
FIG. 8 is an immunoblot showing the protein expression of IRF4 in human cell lines and myeloma patient samples.

Referring to FIG. 8, an immunoblot showing the protein expression of IRF4 in human cell lines and myeloma patient samples is provided. Specific expression of IRF4 in CD138 positive cells isolated from the myeloma patient can be observed. The mononuclear cells from early stage of myeloma, namely monoclonal gammopathy of undetermined significance (MGUS), shows no expression of IRF4.

Figure 9:
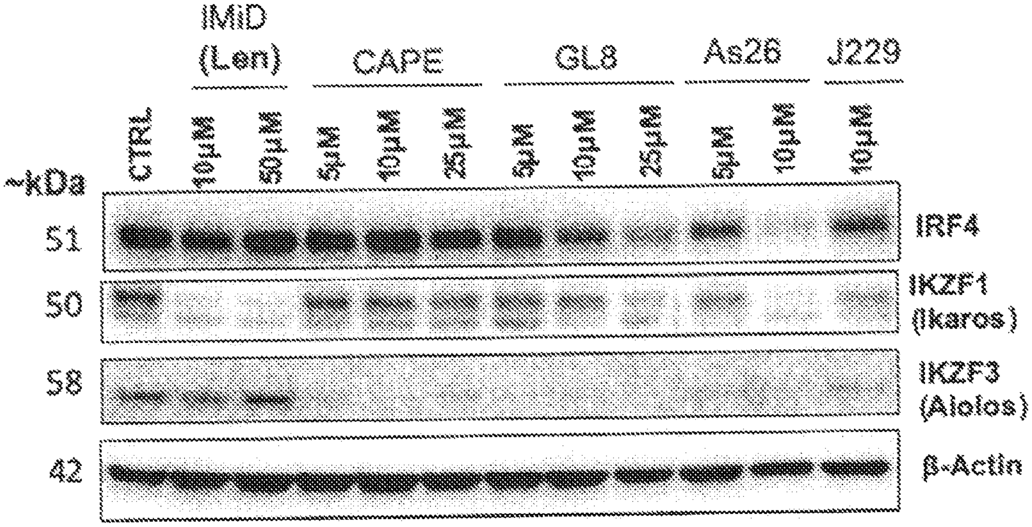
FIG. 9 is an immunoblot showing the effect of lenalidomide (IMiD), CAPE, GL8, As26, and J229 on human myeloma cell line MM1R.

Referring to FIG. 9, an immunoblot showing the effect of lenalidomide (IMiD), CAPE, GL8, As26 and J229 on human myeloma cell line MM1R is provided. Lenalidomide, CAPE and other analogs at indicated concentrations were added to MMIR cells for 48 hours. Proteins extracts from control and treated conditions were subjected to electrophoresis followed by immunoblotting, and membrane probed sequentially using IRF4, IKZF1, IKZF3 and beta-actin antibodies, while beta-actin was used as the protein loading control.

For use in therapy a therapeutically effective amount of As26, J229, J91, LL27, LL23, HM7, As25, MT26, or J205 or pharmaceutically acceptable salts or solvates thereof, may be presented as a pharmaceutical composition. Thus, in a further embodiment the invention provides a pharmaceutical composition of As26, J229, J91, LL27, LL23, HM7, As25, MT26, or J205 or pharmaceutically acceptable salts or solvates thereof in admixture with one or more pharmaceutically acceptable carriers, diluents, or excipients. The carrier(s), diluent(s) or excipient(s) must be acceptable in the sense of being compatible with the other ingredients of the formulation and not deleterious to the recipient thereof.

When applicable, the compositions of the present invention, including As26, J229, J91, LL27, LL23, HM7, As25, MT26, or J205 may be in the form of and/or may be administered as a pharmaceutically acceptable salt.

Typically, a pharmaceutically acceptable salt may be readily prepared by using a desired acid or base as appropriate. The salt may precipitate from solution and be collected by filtration or may be recovered by evaporation of the solvent.

Suitable addition salts are formed from acids which form non-toxic salts and examples are hydrochloride, hydrobromide, hydroiodide, sulphate, nitrate, phosphate, hydrogen phosphate, dihydrogen phosphate acetate, maleate, malate, fumarate, lactate, tartrate, citrate, formate, gluconate, succinate, pyruvate, oxalate, oxaloacetate, trifluoroacetate, saccharinate, benzoate, methanesulphonate, ethanesulphonate, benzenesulphonate, p-toluenesulphonate and isethionate.

Suitable salts may also be formed from bases, forming salts including ammonium salts, alkali metal salts such as those of sodium and potassium, alkaline earth metal salts such as those of calcium and magnesium. Pharmaceutically acceptable salts may also be prepared from other salts, including other pharmaceutically acceptable salts, using conventional methods.

Pharmaceutical compositions of the invention may be formulated for administration by any appropriate route. Therefore, the pharmaceutical compositions of the invention may be formulated, for example, as tablets, capsules, powders, granules, lozenges, creams or liquid preparations, such as oral solutions or suspensions. Such pharmaceutical formulations may be prepared by any method known in the art of pharmacy, for example by bringing into association the active ingredient with the carrier(s) or excipient(s).

Tablets and capsules for oral administration may be in unit dose presentation form, and may contain conventional excipients such as binding agents, for example syrup, acacia, gelatine, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatine, hydroxyethyl cellulose, carboxymethyl cellulose, aluminium stearate gel or hydrogenated edible fats, emulsifying agents, for example lecithin, sorbitan, monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

It should be understood that in addition to the ingredients particularly mentioned above, the formulations may include other agents conventional in the art having regard to the type of formulation in question.

The compositions of the present invention may be suitable for the treatment of diseases in a human or animal patient. In one embodiment, the patient is a mammal including a human, horse, dog, cat, sheep, cow, or primate. In one embodiment the patient is a human. In a further embodiment, the patient is not a human.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein the term "treatment" refers to defending against or inhibiting a symptom, treating a symptom, delaying the appearance of a symptom, reducing the severity of the development of a symptom, and/or reducing the number or type of symptoms suffered by an individual, as compared to not administering a pharmaceutical composition of the invention. The term treatment encompasses the use in a palliative setting The present invention, in another embodiment, relates to a use of a pharmaceutical composition including As26, J229, J91, LL27, LL23, HM7, As25, MT26, or J205 or a pharmaceutically acceptable salt or solvate thereof, together with one or more pharmaceutically acceptable carriers, diluents and excipients for the treatment of blood cancers.

REFERENCES

Abdi J, Chen G, Chang H. (2013) Drug resistance in multiple myeloma: latest findings and new concepts on molecular mechanisms. Oncotarget: 4: 2186-2207.

Armutcu, F., Akyol, S., Ustunsoy, S., & Turan, F. F. (2015). Therapeutic potential of caffeic acid phenethyl ester and its anti-inflammatory and immunomodulatory effects (Review). *Experimental and Therapeutic Medicine,* 9(5), 1582-1588. http://doi.org/10.3892/etm.2015.2346.

Bai B, Wu S, Wang R, Xu J, and Chen L, Bone marrow IRF4 level in multiple myeloma: an indicator of peripheral blood Th17 and disease. Oncotarget, 2017, Vol. 8, (49), pp: 85392-85400

Bertrand E, Jouy N, Manier S, Fouquet G, Guidez S, Boyle E, Noel S, Tomowiak C, Herbaux C, Schraen S, Preudhomme C, Quesnel B, Poulain S and Leleu X, Role of IRF4 in resistance to immunomodulatory (IMid) compounds in Waldenström's macroglobulinemia. Oncotarget, 2017, Vol. 8, (68), pp: 112917-112927.

Boddicker, R. L., Kip, N. S., Xing, X., Zeng, Y., Yang, Z.-Z., Lee, J.-H., Feldman, A. L. (2015). The oncogenic transcription factor IRF4 is regulated by a novel CD30/NF-κB positive feedback loop in peripheral T-cell lymphoma. *Blood,* 125(20), 3118-27. http://doi.org/10.1182/blood-2014-05-578575

Chesi, M., et al., The t(4;14) translocation in myeloma dysregulates both FGFR3 and a novel gene, MMSET, resulting in IgH/MMSET hybrid transcripts. Blood, 1998a. 92(9): p. 3025-34.

Chesi, M., et al., Dysregulation of cyclin D1 by translocation into an IgH gamma switch region in two multiple myeloma cell lines. Blood, 1996. 88(2): p. 674-81.

Chesi, M., et al., Frequent dysregulation of the c-maf proto-oncogene at 16q23 by translocation to an Ig locus in multiple myeloma. Blood,1998b. 91(12): p. 4457-63.

Do, T. N., Ucisik-Akkaya, E., Davis, C. F., Morrison, B. A., & Dorak, M. T. (2010). An intronic polymorphism of IRF4 gene influences gene transcription in vitro and shows a risk association with childhood acute lymphoblastic leukemia in males. *Biochimica et Biophysica Acta,* 1802(2), 292-300. http://doi.org/10.1016/j.bbadis.2009.10.015.

Doiron, J. A., Leblanc, L. M., Hébert, M. J., Levesque, N. A., Pare, A. F., Jean-François, J., Cormier, M., Surette, M. E, Touaibia, M. (2017). Structure-activity relationship of caffeic acid phenethyl ester analogs as new 5-lipoxygenase inhibitors. Chem Biol Drug Des. 89(4): 514-528.

Fesen, M. R., Pommier, Y., Leteurtre, F., Hiroguchi, S., Yung, J., & Kohn, K. W. (1994). Inhibition of HIV-1 integrase by flavones, caffeic acid phenethyl ester (CAPE) and related compounds. *Biochemical Pharmacology,* 48(3), 595-608. Retrieved from http://www.ncbi.nlm.nih.gov/pubmed/7520698.

Greenberg, A., Walters, D., Kumar, S., Rajkumar V., Jelinek, D., Responsiveness of cytogenetically discrete human myeloma cell lines to lenalidomide: Lack of correlation with cereblon and interferon regulatory factor 4 expression levels. *Eur J Haematol.* 2013 December; 91(6): doi:10.1111/ejh.12192.

Lopez-Girona A, Mendy D, Ito T, Miller K, Gandhi AK, Kang J. (2012). Cereblon is a direct protein target for immunomodulatory and antiproliferative activities of lenalidomide and pomalidomide. Leukemia, 26: 2326-2335.

Hengeveld, P. J., & Kersten, M. J. (2015). B-cell activating factor in the pathophysiology of multiple myeloma: a target for therapy? *Blood Cancer Journal,* 5, e282. http://doi.org/10.1038/bcj.2015.3

Iida, S., Rao, P. H., Butler, M., Corradini, P., Boccadoro, M., Klein, B., . . . Dalla-Favera, R. (1997). Deregulation of MUM1/IRF4 by chromosomal translocation in multiple myeloma. *Nature Genetics,* 17(2), 226-30. http://doi.org/10.1038/ng1097-226.

Ito T, Ando H, Suzuki T, Ogura T, Hotta K .Handa H. (2010) Identification of a primary target of thalidomide teratogenicity. Science. March 12; 327(5971):1345 50.

Klein, U., Casola, S., Cattoretti, G., Shen, Q., Lia, M., Mo, T., . . . Dalla-Favera, R. (2006). Transcription factor IRF4 controls plasma cell differentiation and class-switch recombination. *Nature Immunology,* 7(7), 773-82. http://doi.org/10.1038/ni1357

Kyle, R A, Gertz, M A, Witzig, T E, et al. Review of 1027 patients with newly diagnosed multiple myeloma. Mayo Clinic Proceedings 2003; 78(1):21-33

Larki-Harchegani, A., Hemmati, A. A., Arzi, A., Ghafurian-Boroojerdnia, M., Shabib, S., Zadkarami, M. R., & Esmaeilzadeh, S. (2013). Evaluation of the Effects of Caffeic Acid Phenethyl Ester on Prostaglandin E2 and Two Key Cytokines Involved in Bleomycin-induced Pulmonary Fibrosis. *Iranian Journal of Basic Medical Sciences,* 16(7), 850-7. Retrieved from http://www.ncbi.nlm.nih.gov/pubmed/23997916.

Marriott J B, Muller G, Stirling D, Dalgleish A G. (2001) Immunotherapeutic and antitumour potential of thalidomide analogues. Expert Opin Biol Ther., July; 1 (4):675-82.

Matsui W, Wang Q, Barber J P, Brennan S, Smith B D, Borrello I, et al. Clonogenic multiple myeloma progenitors, stem cell properties, and drug resistance. Cancer Res. 2008; 68: 190-197.

Natarajan, K., Singh, S., Burke, T. R., Grunberger, D., & Aggarwal, B. B. (1996). Caffeic acid phenethyl ester is a potent and specific inhibitor of activation of nuclear transcription factor NF-kappa B. *Proceedings of the National Academy of Sciences of the United States of America,* 93(17), 9090-5. Retrieved from http://www.ncbi.nlm.nih.gov/pubmed/8799159.

Nishida, K., et al., *The Ig heavy chain gene is frequently involved in chromosomal translocations in multiple myeloma and plasma cell leukemia as detected by in situ hybridization.* Blood, 1997. 90(2): p. 526-34.

Odqvist, L., Sanchez-Beato, M., Montes-Moreno, S., Martin-Sánchez, E., Pajares, R., Sánchez-Verde, L., . . . Piris, M. A. (2013). NIK controls classical and alternative NF-κB activation and is necessary for the survival of human T-cell lymphoma cells. *Clinical Cancer Research : An Official Journal of the American Association for Cancer Research,* 19(9), 2319-30. http://doi.org/10.1158/1078-0432.CCR-12-3151.

Okutan, H., Ozcelik, N., Yilmaz, H. R., & Uz, E. (2005). Effects of caffeic acid phenethyl ester on lipid peroxidation and antioxidant enzymes in diabetic rat heart. *Clinical Biochemistry,* 38(2), 191-6. http://doi.org/10.1016/j.clinbiochem.2004.10.003.

Onori, P.; DeMorrow, S.; Gaudio, E.; Franchitto, A.; Mancinelli, R.; Venter, J.; Kopriva, S.; Ueno, Y.; Alvaro, D.; Savage, J.; et al. Caffeic acid phenethyl ester decreases cholangiocarcinoma growth by inhibition of NF-κB and induction of apoptosis. Int. J. Cancer 2009, 125, 565-576.

Patel, S. (2016). Emerging Adjuvant Therapy for Cancer: Propolis and its Constituents. *Journal of Dietary Supplements,* 13(3), 245-68. http://doi.org/10.3109/19390211.2015.1008614

Rajkumar S V. Multiple myeloma: 2014 update on diagnosis, risk-stratification, and management. Am J Hematol 2014; 89(10):998-1009.

Ryu, D., Kim, H. J., Joung, J.-G., Lee, H.-O., Bae, J. S., Kim, S. J., . . . Kim, K. (2014). Comprehensive genomic profiling of IgM multiple myeloma identifies IRF4 as a prognostic marker. *Oncotarget,* 7(30). http://doi.org/10.18632/oncotarget.9478

Sanderson, J. T., Clabault, H., Patton, C., Lassalle-Claux, G., Jean-François, J., Paré, A. F., Touaibia, M. (2013). Antiproliferative, antiandrogenic and cytotoxic effects of novel caffeic acid derivatives in LNCaP human androgen-dependent prostate cancer cells. *Bioorganic & Medicinal Chemistry,* 21(22), 7182-93. http://doi.org/10.1016/j.bmc.2013.08.057

Shaffer, A. L., Emre, N. C. T., Lamy, L., Ngo, V. N., Wright, G., Xiao, W., Staudt, L. M. (2008). IRF4 addiction in multiple myeloma. *Nature,* 454(7201), 226-31. http://doi.org/10.1038/nature07064.

Shaughnessy, J., Jr., et al., *Cyclin D3 at 6p21 is dysregulated by recurrent chromosomal translocations to immunoglobulin loci in multiple myeloma.* Blood, 2001. 98(1): p. 217-23.

Shen, H., Yamashita, A., Nakakoshi, M., Yokoe, H., Sudo, M., Kasai, H., . . . Moriishi, K. (2013). Inhibitory effects of caffeic acid phenethyl ester derivatives on replication of hepatitis C virus. *PloS One,* 8(12), e82299. http://doi.org/10.1371/journal.pone.0082299

Singhal S, Mehta J, Desikan R, Ayers D, Roberson P Barlogie B. (1999) Antitumor activity of thalidomide in refractory multiple myeloma. N Engl J Med. November 18; 341(21):1565-71.

Sy, L. B., Yang, L.-K., Chiu, C.-J., & Wu, W.-M. (2011). The immunoregulatory effects of caffeic acid phenethyl ester on the cytokine secretion of peripheral blood mononuclear cells from asthmatic children. *Pediatrics and Neonatology,* 52(6), 327-31. http://doi.org/10.1016/j.pedneo.2011.08.005

Szliszka, E., Czuba, Z. P., Bronikowska, J., Mertas, A., Paradysz, A., & Krol, W. (2011). Ethanolic Extract of Propolis Augments TRAIL-Induced Apoptotic Death in Prostate Cancer Cells. *Evidence-Based Complementary and Alternative Medicine: eCAM,* 2011, 535172. http://doi.org/10.1093/ecam/nep180

Toman I, Loree J, Klimowicz A C, Bahlis N, Lai R, Belch A, Pilarski L, Reiman T. (2011). Expression and prognostic significance of Oct2 and Bob1 in multiple myeloma: implications for targeted therapeutics. Leuk Lymphoma 52(4): 659-67. doi: 10.3109/10428194.2010.548535.

Turesson, I., et al., *Patterns of improved survival in patients with multiple myeloma in the twenty-first century: a population-based study.* Journal of clinical oncology: official journal of the American Society of Clinical Oncology, 2010. 28(5): p. 830-4.

Wang, L., Chu, K., Liang, Y., Lin, Y., & Chiang, B. (2010). Caffeic acid phenethyl ester inhibits nuclear factor-kappaB and protein kinase B signalling pathways and induces caspase-3 expression in primary human CD4+ T cells. *Clinical and Experimental Immunology,* 160(2), 223-32. http://doi.org/10.1111/j.1365-2249.2009.04067.x Wang L, Yao Z Q, Moorman J P, Xu Y, Ning S (2014) Gene Expression Profiling Identifies IRF4-Associated Molecular Signatures in Hematological Malignancies. PLoS ONE 9(9): e106788. doi:10.1371/journal-.pone.0106788.

Wang L, Toomey N L, Diaz L A, Walker G, Ramos J C, et al. (2011) Oncogenic IRFs provide a survival advantage for EBV- or HTLV1-transformed cells through induction of BIC expression. J Virol 85: 8328-8337.

Watabe, M., Hishikawa, K., Takayanagi, A., Shimizu, N., & Nakaki, T. (2004). Caffeic acid phenethyl ester induces apoptosis by inhibition of NFkappaB and activation of Fas in human breast cancer MCF-7 cells. *The Journal of Biological Chemistry,* 279(7), 6017-26. http://doi.org/10.1074/jbc. M306040200.

Xu D, Zhao L, Del Valle L, Miklossy J, Zhang L (2008) Interferon regulatory factors 4 is involved in Epstein-Barr virus-mediated transformation of human B lymphocytes. J Virol 82: 6251-6258.

Zhu Y X, Kortuem K M, Stewart A K. Molecular mechanism of action of immune-modulatory drugs thalidomide, lenalidomide and pomalidomide in multiple myeloma. Leuk Lymphoma. 2013; 54: 683-687.

We claim:

1. A method for inhibiting the growth of blood cancer cells comprising:

contacting the cells with a caffeic acid phenpropyl ester (GL8) analogue selected from the group consisting of As26, J229, J91, LL27, LL23, As25, MT26, and J205, having the structures:

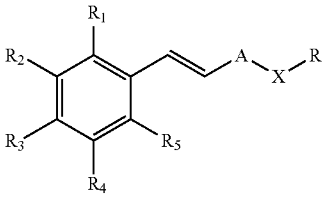

where,

As26: $R_2 = R_3 = R_5 = H$, $R_1 = R_4 = OH$, A = CO, X = O, R = $(CH_2)_3$ Ph
J229: $R_1 = R_4 = R_5 = H$, $R_2 = R_3 = OH$, A = $CH_2$, X = O, R = $(CH_2)_3$ Ph
J91: $R_1 = R_4 = R_5 = H$, $R_2 = R_3 = OH$, A = CO, X = O, R = $CH_2CCPh$
LL27: $R_1 = R_4 = R_5 = H$, $R_2 = R_3 = OH$, A = CO, X = O, R = $(CH_2)_5$ Ph
LL23: $R_1 = R_4 = R_5 = H$, $R_2 = R_3 = OH$, A = CO, X = O, R = $(CH_2)_4$ Ph
As25: $R_3 = R_4 = R_5 = H$, $R_1 = R_2 = OH$, A = CO, X = O, R = $(CH_2)_3$ Ph
MT26: $R_1 = R_4 = R_5 = H$, $R_2 = R_3 = OH$, A = CO, X = O, R = $CH_2CH_2$ Ph(4-F)
J205: $R_1 = R_4 = R_5 = H$, $R_2 = R_3 = OH$, A = CO, X = $CH_2$, R = $(CH_2)_2$ Ph in an amount effective to inhibit the growth.

2. The method of claim 1, wherein the blood cancer cells are myeloma cells.

3. The method of claim 1, wherein the myeloma cells are immunomodulatory drug (IMiD) resistant.

4. The method of claim 1, wherein the myeloma cells are lenalidomide resistant.

5. The method of claim 1, wherein the blood cancer cells are lymphoma cells.

6. The method of claim 5, wherein the lymphoma cells are diffused large B-cell Lymphoma.

7. The method of claim 5, wherein the lymphoma cells are lenalidomide resistant.

8. The method of claim 5, wherein the lymphoma cells are immunomodulatory drug resistant.

9. The method of claim 1, wherein the blood cancer cells are leukemia cells.

10. A method for inhibiting the growth of blood cancer cells in a patient comprising:

administering to a patient a therapeutically effective amount of a caffeic acid phenpropyl ester (GL8) analogue selected from the group consisting of As26, J229, J91, LL27, LL23, As25, MT26, and J205, having the structures:

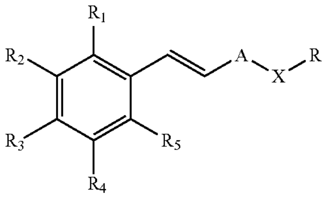

where,

As26: $R_2 = R_3 = R_5 = H$, $R_1 = R_4 = OH$, A = CO, X = O, R = $(CH_2)_3$ Ph
J229: $R_1 = R_4 = R_5 = H$, $R_2 = R_3 = OH$, A = $CH_2$, X = O, R = $(CH_2)_3$ Ph
J91: $R_1 = R_4 = R_5 = H$, $R_2 = R_3 = OH$, A = CO, X = O, R = $CH_2CCPh$
LL27: $R_1 = R_4 = R_5 = H$, $R_2 = R_3 = OH$, A = CO, X = O, R = $(CH_2)_5$ Ph
LL23: $R_1 = R_4 = R_5 = H$, $R_2 = R_3 = OH$, A = CO, X = O, R = $(CH_2)_4$ Ph
As25: $R_3 = R_4 = R_5 = H$, $R_1 = R_2 = OH$, A = CO, X = O, R = $(CH_2)_3$ Ph
MT26: $R_1 = R_4 = R_5 = H$, $R_2 = R_3 = OH$, A = CO, X = O, R = $CH_2CH_2$ Ph(4-F)
J205: $R_1 = R_4 = R_5 = H$, $R_2 = R_3 = OH$, A = CO, X = $CH_2$, R = $(CH_2)_2$ Ph.

11. The method of claim 10, wherein the blood cancer cells are myeloma cells.

12. The method of claim 10, wherein the myeloma cells are immunomodulatory drug (IMiD) resistant.

13. The method of claim 10, wherein the myeloma cells are lenalidomide-resistant.

14. The method of claim 10, wherein the blood cancer cells are lymphoma cells.

15. The method of claim 14, wherein the lymphoma cells are diffused large B-cell Lymphoma.

16. The method of claim 14, wherein the lymphoma cells are lenalidomide resistant.

17. The method of claim 14, wherein the lymphoma cells are immunomodulatory drug resistant.

18. The method of claim 10, wherein the blood cancer cells are leukemia cells.

19. The method of claim 10, wherein the caffeic acid phenpropyl ester (GL8) analogue is As26 having the structure:

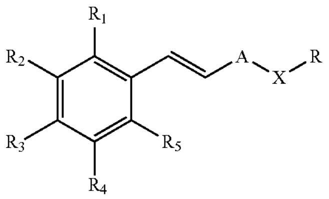

where $R_2=R_3=R_5=H, R_1=R_4=OH, A=CO, X=O, R=(CH_2)_3$ Ph.

20. The method of claim 10, wherein the caffeic acid phenpropyl ester (GL8) analogue is J229 having the structure:

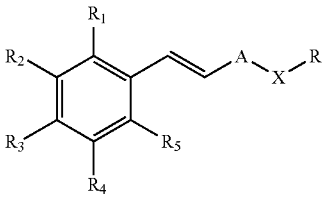

where $R_1=R_4=R_5=H, R_2=R_3=OH, A=CH_2, X=O, R=(CH_2)_3$ Ph.

21. The method of claim 19, wherein the administered therapeutically effective amount decreases a cereblon pathway gene or protein in the patient.

22. The method of claim 20, wherein the administered therapeutically effective amount decreases a cereblon pathway gene or protein in the patient.

* * * * *